United States Patent [19]

Matuzaki et al.

[11] Patent Number: 5,214,184
[45] Date of Patent: May 25, 1993

[54] METHOD OF PRODUCING CARBONIC ACID DIESTER

[75] Inventors: Tokuo Matuzaki; Tsuneo Simamura; Satoru Fujitsu; Yosinobu Toriyahara, all of Ube, Japan

[73] Assignee: Ube Industries, Ltd., Yamaguchi, Japan

[21] Appl. No.: 850,678

[22] Filed: Mar. 13, 1992

[30] Foreign Application Priority Data

Mar. 15, 1991 [JP] Japan .................................. 3-128832
Mar. 26, 1991 [JP] Japan .................................. 3-132375

[51] Int. Cl.$^5$ .............................................. C07C 69/96
[52] U.S. Cl. ...................................................... 558/277
[58] Field of Search .......................................... 558/277

[56] References Cited

FOREIGN PATENT DOCUMENTS

425197A3 5/1991 European Pat. Off. .

OTHER PUBLICATIONS

Japanese Patent Abstract, vol. 4, No. 190 (C-37) (672), Dec. 26, 1980, corresponding to Japanese Patent Appln. No. 54-37349.
Japanese Patent Abstract, vol. 9, No. 211 (C-300) (1934), Aug. 29, 1985, corresponding to Japanese Patent Appln. No. 58-182362.

*Primary Examiner*—José G. Dees
*Assistant Examiner*—Joseph M. Conrad
*Attorney, Agent, or Firm*—Finnegan, Henderson, Farabow, Garrett & Dunner

[57] ABSTRACT

A carbonic acid diester is produced at a high stability and selectivity by catalytically reacting carbon monoxide with a nitrous acid ester in gas phase in the presence of a solid catalyst comprising a catalytic solid material carried on a solid carrier and comprising:

(1) a first component consisting of a platinum group metal or a compound thereof,
(2) a second component consisting of a compound of Fe, Cu, Bi, Co, Ni or Sn,
(3) a third component consisting of a compound of V, Mo or W, and
(4) a fourth component consisting of a halides, for example, fluorides or chlorides, organic acid salts, for example, formates or acetates, or phosphates of an alkali or alkaline earth metal.

28 Claims, 5 Drawing Sheets

Fig. 2

Fig. 3
X-RAY DIFFRACTION PATTERN

Fig. 5

ESCA SPECTRUM

Fig. 6

ESCA SPECTRUM

METHOD OF PRODUCING CARBONIC ACID DIESTER

BACKGROUND OF THE INVENTION

1. Field of the Invention

The present invention relates to a method of producing a carbonic acid diester.

More particularly, the present invention relates to a process of producing a carbonic acid diester selectively and stably from carbon monoxide and a nitrous acid ester.

The carbonic acid diester is very useful as a starting material of medicines and pesticides, and as an intermediate compound of a polycarbonate and urethane.

2. Description of the Related Arts

A conventional method of producing a carbonic acid diester by a reaction of phosgene with an alcohol is well known, and has been practiced for some time. Nevertheless, this conventional method is disadvantageous in that phosgene has an extremely strong toxicity, and the reaction of phosgene with an alcohol produces hydrochloric acid as a by-product, which corrodes the reaction device.

Therefore, there is a strong demand for a new method of producing a carbonic acid diester without using phosgene.

In response to this demand, various attempts have been made to produce a carbonic acid diester from an alcohol and carbon monoxide, as disclosed in, for example, Japanese Unexamined Patent Publication (JP-A) No. 60-75447, 63-72650, and 63-38010, and PCT-Publication No. WO-87/7601.

In those methods, the carbonic acid diester is produced by a catalytic oxygen-oxidizing reaction of carbon monoxide with an alcohol in a liquid phase, in the presence of a catalyst consisting of a copper halide or palladium halide.

These methods are disadvantageous in that, in the catalytic oxygen-oxidizing reaction, carbon dioxide is produced as a by-product, and thus the production of the carbonic acid diester is effected with a low selectivity based on the amount of carbon monoxide supplied to the reaction system. Also, the catalytic oxygen-oxidizing reaction produces water ($H_2O$) as another by-product, and thus the resultant carbonic acid diester must be isolated from the water by a refining procedure. Also, the above-mentioned methods are further disadvantageous in that the aimed carbonic acid diester must be separated from the catalyst in the reaction system.

Accordingly, the above-mentioned methods are not satisfactory for industrial use.

There have been attempts made to eliminate the above-mentioned disadvantages, and as one such attempt, JP-A-60-181051 discloses a method of producing carbonic acid diester by a catalytic oxidizing reaction of a nitrous acid ester with carbon monoxide, in a gas phase, in the presence of a catalyst composed of a solid platinum group metal or compound thereof carried on a solid carrier and an oxidant in an amount of 10 molar % in terms of $O_2$, per mole of carbon monoxide present in the reaction mixture.

In this method, the oxidant in the above-mentioned specific amount based on the carbon monoxide effectively inhibits a production of oxalic acid diester as a by-product, but the addition of the oxidant in the above-mentioned specific acid based on the amount of the carbon monoxide cannot completely inhibit the production of the oxalic acid diester, and therefore, the aimed carbonic acid diester is produced with an unsatisfactorily low selectivity and at an unsatisfactorily low reaction rate.

Further, the above-mentioned method is further disadvantageous in that the proportion of nitrous acid ester in a reaction mixed gas comprising the nitrous acid ester, carbon monoxide, alcohol and oxygen is higher than an explosion (flammable) limit of the mixed gas, and thus this reaction mixed gas is not preferable in view of the safety of the procedure.

Accordingly this method is not satisfactory for practical use.

As mentioned above, the conventional method of producing carbonic acid diester from a nitrous acid ester and carbon monoxide is disadvantageous in that the reaction rate of carbon monoxide with nitrous acid ester is unsatisfactorily low and the selectivity of the resultant carbon acid diester is low, and thus the resultant carbon acid diester must be recovered through complicated purifying procedures. Also, this method is further disadvantageous in that the nitrous acid ester must be employed in a higher content than the explosion limit of the reaction mixed gas, and thus the reaction procedure is dangerous.

SUMMARY OF THE INVENTION

An object of the present invention is to provide a method of producing a carbonic acid diester from a nitrous acid ester and carbon monoxide by a gas phase reaction procedure by which the resultant carbonic acid diester can be easily isolated and corrected from the reaction system.

Another object of the present invention is to provide a method of producing a carbonic acid diester by a catalytic reaction of a nitrous acid ester with carbon monoxide in a gas phase under moderate and safe reaction conditions.

Still another object of the present invention is to provide a method of producing a carbonic acid diester with a high selectivity and an excellent yield from a nitrous acid ester and carbon monoxide in a gas phase, and with a high stability.

A further object of the present invention is to provide a method of producing a carbonic acid diester from nitrous acid ester and carbon monoxide in a gas phase in the presence of a solid catalyst having a highly stable catalytic activity for a long time, and thus this method is useful for a practical gas phase reaction of the nitrous acid ester with carbon monoxide in the presence of a fixed catalyst bed.

The above-mentioned objects can be attained by the method of present invention of producing a carbonic acid diester, comprising the steps of (A) catalytically reacting carbon monoxide with a nitrous acid ester in a gas phase in the presence of a solid catalyst comprising a solid carrier and a catalytically active solid material carried on the solid carrier and comprising:

(1) a first catalyst component consisting of at least one member selected from the group consisting of platinum group metals and compounds thereof;

(2) a second catalyst component consisting of at least one member selected from the group consisting of iron compounds, copper compounds, bismuth compounds, cobalt compounds, nickel compounds and tin compounds;

(3) a third catalyst component consisting of at least one member selected from the group consisting of vanadium compounds, molybdenum compounds and tungsten compounds; and (4) a fourth catalyst component consisting of at least one member selected from alkali metal compounds and alkaline earth metal compounds, and (B) collecting the resultant carbon acid diester from a reaction mixture discharged from the catalytic reaction step (A).

DESCRIPTION OF THE PREFERRED EMBODIMENTS

In the method of the present invention, a nitrous acid ester is reacted with carbon monoxide in a gas phase in the presence of a specific solid catalyst to produce a carbon acid diester.

The nitrous acid ester usable for the method of the present invention is preferably selected from the group consisting of nitrites of lower aliphatic monohydric alcohols having 1 to 4 carbon atoms, for example, methyl nitrite, ethyl nitrite, n-propyl nitrite, isopropyl nitrite, n-butyl nitrite, isobutyl nitrite and sec-butyl nitrite; nitrites of cycloaliphatic monohydric alcohols, for example, cyclohexyl nitrite; and nitrites of aralkyl monohydric alcohols, for example, benzyl nitrite and phenylethyl nitrite.

Among the above-mentioned nitrous acid esters, the nitrites of aliphatic monohydric alcohols having 1 to 4 carbon atoms are preferable for the present invention, and the most preferable nitrous acid esters for the present invention are methyl nitrite and ethyl nitrite.

The solid catalyst usable for the present invention comprises a solid carrier and a catalytically active solid material carried on the solid carrier.

The catalytic solid material comprises (1) a first catalyst component consisting of at least one member selected from the group consisting of platinum group metals, for example, palladium, platinum, iridium, ruthenium and rhodium, and compounds of the platinum group metals, preferably platinum group metal compounds;

(2) a second catalyst component consisting of at least one member selected from the group consisting of iron compounds, copper compounds, bismuth compounds, cobalt compounds, nickel compounds and tin compounds;

(3) a third catalyst component consisting of at least one member selected from the group consisting of vanadium compounds, molybdenum compounds and tungsten compounds; and (4) a fourth catalyst component consisting of at least one member selected from the group consisting of alkali metal compounds and alkaline earth metal compounds.

The platinum group metal compounds usable for the first catalyst component include halides, for example, chlorides, bromides, iodides and fluorides, nitrates, sulfates, phosphates, acetates, oxalates and benzoates of the platinum group metals.

The platinum group compounds preferably selected from the group consisting of palladium chloride, palladium bromide, palladium iodide, palladium fluoride, palladium nitrate, palladium sulfate, palladium phosphate, palladium acetate, palladium oxalate, palladium benzoate, platinum chloride, iridium chloride, ruthenium chloride, ruthenium iodide, rhodium chloride, rhodium bromide, rhodium iodide, rhodium nitrate, rhodium sulfate and rhodium acetate. Among the above-mentioned, the halides and sulfates of palladium, ruthenium and rhodium are particularly preferable for the present invention, but the most preferable compound for the first catalyst component is palladium chloride.

The metal compounds usable for the second catalyst component include halides, for example, chlorides, bromides, iodides, and fluorides, nitrates, sulfates, phosphates, acetates of iron, copper, bismuth, cobalt, nickel and tin, and the preferable compounds are halides of the above-mentioned compounds.

The third catalyst component preferably consist of at least one member selected from the group consisting of oxides, metal acids, metal salts of metal acids and ammonium salts of metal acids of vanadium, molybdenum and tungsten. Among the above-mentioned metal compounds, metal oxides, namely vanadium oxide, molybdenum oxide and tungsten oxide, and ammonium salts of metal acids, for example, ammonium vanadate, ammonium molybdate and ammonium tungstate.

The fourth catalyst component preferably consists of at least one member selected from halides, for example, fluorides and chlorides, of alkali metals and organic acids salts and phosphates of alkali metals and alkaline earth metals.

In an embodiment of the present invention, the fourth catalyst component consists of at least one member selected from the group consisting of fluorides of alkali metals, for example, lithium fluoride, sodium fluoride, potassium fluoride, rubidium fluoride and cesium fluoride.

In another embodiment of the present invention, the fourth catalyst component consists of at least one member selected from the group consisting of alkali metal salts and alkaline earth metal salts of organic acids.

The organic acids usable for the present invention include lower aliphatic mono-carboxylic acids, for example, formic acid and acetic acid.

The organic acid salts usable for the fourth catalyst component are preferably selected from the group consisting of lithium formate, sodium formate, potassium formate, rubidium, cesium formate, sodium acetate, potassium acetate, rubidium acetate, cesium acetate, magnesium formate, calcium formate, strontium formate, barium formate, magnesium acetate, calcium acetate, strontium acetate and barium acetate.

In still another embodiment of the present invention, the fourth catalyst component consists of at least one member selected from chlorides of alkali metals, for example, lithium chloride, sodium chloride, potassium chloride, rubidium chloride and cesium chloride.

In still another embodiment of the present invention, the fourth catalyst component consists of at least one member selected from the group consisting of phosphates of alkali metals and alkaline earth metals, for example, lithium phosphate, dilithium hydrogen phosphate, lithium dihydrogen phosphate, sodium phosphate, disodium hydrogen phosphate, sodium dihydrogen phosphate, potassium phosphate, dipotassium hydrogen phosphate, potassium dihydrogen phosphate, rubidium phosphate, dirubidium hydrogen phosphate, rubidium dihydrogen phosphate, cesium phosphate, dicesium hydrogen phosphate, cesium dihydrogen phosphate, magensium phosphate, magnesium hydrogen phosphate, magnesium dihydrogen phosphate, calcium phosphate, calcium hydrogen phosphate, calcium dihydrogen phosphate, strontium phosphate, strontium hydrogen phosphate, strontium dihydrogen phosphate, barium phosphate, barium hydrogen phosphate, and barium dihydrogen phosphate.

The solid carrier usable for the method of the present invention preferably comprises at least one member selected from the group consisting of diatomaceous earth, activated carbon, silicon carbide, titania, alumina and silica-alumina. The activated carbon is the most preferable material for the solid carrier.

The catalytically active solid material can be carried on the solid carrier by a conventional application method, for example, an impregnating method in which the solid carrier is immersed in a dispersion of the catalytic solid material in the form of fine particles, so that the catalytic solid material particles are allowed to be adsorbed by the solid carrier, a mix-kneading method in which a mixture of grains of the solid carrier and fine particles of the catalytic solid material is kneaded so that the catalytic solid material particles are adhered to the solid carrier grains, a deposition method in which fine particles of the catalytic solid particles are deposited on the solid carrier grains, an evaporate-drying method in which a dispersion of the catalytic solid material in a volatile solvent is applied to solid carrier grains and then the resultant product is dried by evaporating away the volatile solvent, or a co-precipitation method in which the solid carrier and the catalytic solid material are co-precipitated from a solution thereof so that the precipitated catalytic solid material in the form of fine particles is carried on the precipitated solid carrier in the form of grains or particles.

Preferably, in the preparation of the solid catalyst of the present invention, the impregnating method and the evaporate-drying method are utilized.

In the preparation of the solid catalyst, the first to fourth catalyst components may be carried at one time or successively stepwise.

In the solid catalyst of the present invention, the first catalyst component is preferably present in an amount, in terms of the platinum group metal as used, of 0.1% to 10% by weight, more preferably 0.5% to 2% by weight, based on the weight of the solid carrier.

Also, the second catalyst component preferably present in an amount, in terms of the metal as used, of 0.1 to 50 gram atom equivalents, more preferably 1 to 10 gram atom equivalents, per gram atom equivalent of the first catalyst component in terms of the platinum group metal contained therein.

Further, the third catalyst component is preferably present in an amount, in terms of the metal as used, of 0.1 to 20 gram atom equivalents, more preferably 0.5 to 5 gram atom equivalents, per gram atom equivalent of the first catalyst component in terms of the platinum group metal contained therein.

Furthermore, the fourth catalyst component is preferably present in an amount, in terms of the metal as used, of 0.1 to 20 gram atom equivalent, more preferably 0.5 to 10 gram atom equivalent, per gram atom equivalent of the first catalyst component in terms of the platinum group metal contained therein.

In the solid catalyst of the present invention, the second catalyst component consisting of at least one member selected from iron compounds, copper compounds, bismuth compounds, cobalt compounds, nickel compounds and tin compounds, serves as a promoter for the reaction of the nitrous acid ester with carbon monoxide. Namely, when the second catalyst component is used in combination with the first catalyst component consisting of at least one member selected from platinum group metals and compounds thereof, in the specific amount as mentioned above, the reaction rate of the nitrous acid ester with carbon monoxide is significantly increased in comparison with that when the second catalyst component is not employed.

When the third catalyst component consisting of at least one member selected from vanadium compounds, molybdenum compounds and tungsten compounds is used in the specific amount as mentioned above, the resultant solid catalyst exhibits a very low deactivation rate, and thus has an excellent catalytic activity durability.

Further, when the fourth catalyst component consisting of at least one member selected from alkali metal compounds and alkaline earth metal compounds, is used in the specific amount as mentioned above, the resultant solid catalyst exhibits a further decreased deactivation rate, and thus has an excellent catalytic activity durability.

Usually, the solid catalyst usable for the present invention is in the form of fine particles, coarse particles, grains or other shapes. There is no limitation of the size of the solid catalyst.

Preferably, the solid catalyst in the form of fine particles has a size of from 20 to 100 μm.

Also, the solid catalyst in the form of coarse particles preferably has a mesh size of from 4 to 200.

Further, the solid catalyst in the form of grains or shaped articles preferably has a size of 1 to 30 mm.

When the specific solid catalyst of the present invention is employed, the catalytic reaction of a nitrous acid ester with carbon monoxide can be effectively conducted even under moderate conditions; this is one of the advantages of the method of the present invention. For example, the catalytic reaction in the method of the present invention can be effected at a temperature of from 0° C. to 200° C., preferably from 50° C. to 140° C., under the ambient atmospheric pressure or more, for example, 1 to 20 kg/cm$^2$G.

Preferably, the catalystic reacting step is carried out at a temperature of 50° C. to 140° C. under an ambient atmospheric pressure.

The nitrous acid ester usable as a starting substance for the method of the present invention can be easily prepared, for example, by decomposing sodium nitrite in an aqueous solution in the presence of nitric acid or sulfuric acid to generate a mixed gas of nitrogen monoxide (NO) and nitrogen dioxide (NO$_2$), oxidizing a portion of the nitrogen monoxide in the mixed gas with molecular oxygen to convert same to nitrogen dioxide and to provide a NOx gas having a molar ratio of nitrogen monoxide to nitrogen dioxide, NO/NO$_2$, of 1/1, and bringing the NOx gas into contact with an alcohol.

When the preparation step of the nitrous acid ester is followed by the production step of the carbonic acid diester, the catalytic reaction of the nitrous acid ester with carbon monoxide is preferably carried out under a slightly higher pressure than the ambient atmospheric pressure, for example, 2 to 3 kg/cm²G.

The catalytic reaction step of the nitrous acid ester with carbon monoxide can be carried out in a batch system or a continuous reaction system. The continuous reaction system is advantageous for an industrial production of the carbonic acid diester.

In any reaction system, the solid catalyst of the present invention may be placed in a fixed catalyst bed or a fluidized catalyst bed of a reactor.

In the method of the present invention, the starting materials, i.e., carbon dioxide and a nitrous acid ester, are fed in a gas phase into a reactor. In this feed gas, the starting materials are preferably diluted with an inert gas, for example, a nitrogen, argon or carbon dioxide gas.

The feed gas for the catalytical reaction step need not have a specific composition, but from the viewpoint of safety, the feed gas preferably has a content of the nitrous acid ester of 20% by volume or less, more preferably, 5 to 20% by volume. Also, from the viewpoint of economy, the content of carbondioxide in the feed gas is from 5% to 20% by volume.

After the catalytic reaction step is completed non-reacted portions of the nitrous acid ester and carbon monoxide are preferably returned to the catalytic reaction step, and a portion of the returned gas is purged to the outside of the reactor.

Usually, carbon monoxide is consumed at a relatively low conversion rate of 20% to 30% by volume, and therefore, a content of carbon monoxide of more than 20% by volume does not bring any advantage but results in a lower efficiency. Also, a content of carbon monoxide of less than 5% by volume brings an unsatisfactory productivity. Nevertheless, if this low economic efficiency is ignored, the carbon monoxide may be employed in a content of more than 20% by volume, for example, up to 80% by volume. In this case, the portion of carbon monoxide above 20% by volume serves as a dilute gas, in place of the inert gas, for the nitrous acid ester.

In the method of the present invention, the feed gas preferably contains carbon monoxide in a molar ratio to a nitrous acid ester of 0.1/1 to 10/1, more preferably 0.25/1 to 1/1.

Also, in the method of the present invention, the feed gas containing the nitrous acid ester and carbon monoxide is preferably fed into the catalytic reaction step at a space velocity of 500 to 20,000 hr⁻¹, more preferably 2,000 to 15,000 hr⁻¹.

In the catalytic reaction step, the reaction of the nitrous acid ester with carbon monoxide produces nitrogen monoxide (NO) as a by-product. Therefore, after the completion of the catalytic reaction step, nitrogen monoxide gas is preferably recovered from the resultant gas mixture of the catalytic reaction and then fed to the step of providing a NOx gas and utilized for the reaction of an alcohol with the NOx gas to produce a nitrous acid ester.

Also, the resultant reaction mixture of the catalytic reaction step contains, in addition to the aimed carbonic acid diester, oxalic acid diester as a by-product, non-reacted nitrous acid ester and carbon monoxide, carbon dioxide as a by product, and an inert dilute gas.

Then the aimed carbonic acid diester is collected by cooling the resultant reaction mixture at a temperature of from −10° C. to 10° C. and removing non-condensed gas comprising carbon monoxide, nitrous acid ester, nitrogen monoxide, carbon dioxide and inert dilute gas.

A portion of the removed non-condensed gas is purged to the outside of the reaction system, and the remaining portion of the removed non-condensed gas is reused for the production of the nitrous acid ester and the carbonic acid diester.

The condensed liquid obtained from the cooling procedure is used to recover the aimed carbonic acid diester by a customary refining process, for example, distillation.

As mentioned above, the nitrous acid ester usable for the method of the present invention is prepared by a reaction of an alcohol with nitrogen oxides, optionally in the presence of molecular oxygen. Therefore, the resultant product intoins, in addition to the nitrous acid ester, non-reacted alcohol, nitrogen oxides (mainly nitrogen monoxide) and sometimes a small amount of water and/or oxygen.

In the method of the present invention, the above-mentioned nitrous acid ester-containing gas can be used as a nitrous acid ester-supply source without any difficulty and disadvantage.

In a further embodiment of the process of the present invention, palladium tetramine molybdate is used as the first and third catalyst component.

As results of an elemental analysis, infra-red spectrum analysis and ESCA spectrum analysys, it is established that the palladium tetramine molybdate has the chemical formula:

$$Pd(NH_3)_4MoO_4 \cdot H_2O$$

The palladium tetramine molybdate is prepared by reacting a molybdate with a palladium salt in a molar ratio of from 0.2 : 1 to 5.0 : 1 in an aqueous ammonium solution. The reaction is carried out, for example, in accordance with the following chemical equation:

$$PdCl_3 + Na_2MoO_4 + 4NH_4OH$$
$$= Pd(NH_3)_4MoO_4 \cdot H_2O + 2NaCl + 3H_2O$$

The palladium salt usable for the reaction is preferably selected from the group consisting of palladium halides, for example, palladium chloride palladium bromide, palladium iodide and palladium fluoride, palladium nitrates, palladium sulfates and palladium acetate, more preferably, from palladium chloride, palladium bromide, palladium nitrate, and palladium sulfate.

The molybdate usable for the preparation of palladium tetramine molybdate is preferably selected from the group consisting of alkali metal molybdates, for example, Li, Na, K, Rb and Cs molybdates, and ammonium molybdate, more preferably from sodium molybdate, potassium molybdate and ammonium molybdate.

In the above-mentioned reaction, the molar ratio of the molybdate to the palladium salt is 0.2 : 1 to 5.0 : 1, preferably 0.5 : 1 to 1.5 : 1.

The reaction of the molybdate with the palladium salt is carried out in an aqueous ammonia solution. This solution preferably has a concentration of ammonia of 5 to 25% by weight, more preferably 14 to 25% by weight. The aqueous ammonia solution is employed in an amount high enough to completely dissolve the total amount of the molybdate and the palladium salt.

The molybdate, the palladium salt and the aqueous ammonia solution can be mixed in any order. Preferably, the palladium salt is dissolved in the aqueous ammonia solution, the molybdate is separately dissolved in the aqueous ammonia solution, and then the palladium salt solution and the molybdate solution are simultaneously, gradually added to the aqueous ammonia solution. Alternatively, the molybdate solution is gradually added to the palladium salt solution.

The reaction is preferably carried out at a boiling temperature of water or less, more preferably from −10° C. to 100° C., still more preferably from 10° C. to 100° C., under the ambient atmospheric pressure or more. The reaction time is usually 5 minutes to 5 hours.

When the molar ratio of the molybdate to the palladium salt is 0.5 : 1 to 1.5 : 1, the reaction product comprises an aimed palladium triamine molybdate which is substantially insoluble in the aqueous ammonia solution at room temperature or less. Therefore, the aimed compound is easily collected from the reaction mixture, by filtration.

The palladium tetramine molybdate is useful as a catalyst component for producing, at a high selectivity and a high stability, a carbonic acid diester from carbon monoxide and a nitrous acid ester, succinic acid diester from ethylene, carbon monoxide and a nitrous acid ester, 3,3-dimethoxypropionitrile from acrylonitrile and methyl nitrite, and other useful compounds from an unsaturated organic compound, carbon monoxide and nitrous acid ester.

The palladium tetramine molybdate is preferably used in an amount, in terms of palladium contained therein, of 0.1 to 10% by weight, more preferably 0.5 to 2% by weight, based on the weight of the solid carrier.

EXAMPLES

The present invention will be further explained by the following specific examples.

In the examples, the space time yield (STY) in g/l·hr of the resultant product was calculated in accordance with the following equation:

$$Y = a/(b \times \theta)$$

wherein Y represents a space time yield in g/l·hr of the product, $\theta$ represents a reaction time in hours of carbon monoxide with a nitrous acid ester, a represents a weight in grams of the resultant carbonic acid diester during the reaction time $\theta$, and b represents a volume in liters of a solid catalyst present in the reaction step (or reaction tube).

Also, in the examples, the catalytic activity reduction coefficient of a catalyst was calculated in accordance with the following equations:

$$Y_t = Y_o \cdot exp(-kt)$$

$$Da = 100 \times k$$

wherein Da represent a catalytic activity reduction coefficient in $hr^{-1}$ of the catalyst under predetermined reaction conditions, Yo represents a space time yield in g/l·hr of the product in an initial stage of the reaction procedure, i.e., 2 hours after the start of the reaction, Yt represents a space time yield in g/l·hr of the product at t hours after the start of the reaction, and k is a constant obtained from the equation $Y_t = Y_o \cdot exp(-kt)$.

EXAMPLE 1

Preparation of Catalyst

A catalyst component aqueous solution containing Pd, Cu, Mo and potassium fluoride was prepared by heat-dissolving 0.33 g of palladium chloride ($PdCl_2$), 0.641 g of cupric chloride ($CuCl_2 \cdot 2H_2O$), 0.679 g of ammonium molybdate [$(NH_4)_6Mo_7O_{24} \cdot 4H_2O$] and 0.218 g of potassium fluoride in 70 ml of an aqueous solution of 25% by weight of ammonia at a temperature of 80° C to 90° C.

Separately, 20 g of particulate activated carbon (C) having a size of 0.5 to 0.7 mm was immersed and dispersed in 50 ml of an aqueous solution of 25% by weight of ammonia, then the above-mentioned catalyst component solution was mixed with the activated carbon dispersion. The resultant mixture was left to stand for one hour.

The mixture was then subjected to water evaporation at a temperature of 80° C. under a reduced pressure, and dried in a nitrogen gas atmosphere at a temperature of 200° C. to provide a solid catalyst.

The resultant solid catalyst had an empirical composition of $PdCl_2$-$CuCl_2$-$(NH_4)_6Mo_7O_{24}$-KF/C (activated carbon).

The first catalyst component was present in an amount in terms of metallic palladium of 1% based on the weight of the solid carrier consisting of the activated carbon.

The content ratio in atom equivalent of the first, second, third and fourth catalyst components were Pd : Cu : Mo : KF = 1 : 2 : 2.1 : 2.

Production of a Carbonic Acid Diester

The above-mentioned solid catalyst in an amount of 1.5 ml was placed in a gas phase reaction tube having an inside diameter of 20 mm and equipped with an outside heating jacket. The reaction tube filled by the solid catalyst was fixed vertically and a heating medium consisting of a silicone oil was made to flow through the outside heating jacket to maintain the inside temperature of the reaction tube at a level of 120° C.

A mixed gas consisting of 8% by volume of methyl nitrite, 8% by volume of carbon monoxide, 3% by volume of nitrogen monoxide, 10% by volume of methyl alcohol and 71% by volume of nitrogen was Fed into the reaction tube through a top end thereof at a space velocity (GHSV) of 15000 $hr^{-1}$ under the ambient atmospheric pressure. The methyl nitrite was produced from nitrogen monoxide, oxygen and methyl alcohol.

In the reaction tube, the methyl nitrite reacted with carbon monoxide in the presence of the solid catalyst.

The resultant reaction mixture discharged from the reaction tube through a bottom thereof was made to flow through methyl alcohol cooled with ice, to collect the resultant reaction product. The collected reaction product was subjected to gas chromatography, and it was confirmed that at 2 hours after the start of the reaction procedure, the space time yield (STY) of dimethyl carbonate was 490 g/l·hr, and at 9 hours after the start of the reaction procedure, the STY of dimethyl carbonate was 477 g/l·hr. Thus, the solid catalyst exhibited a catalytic activity reduction coefficient Da of 0.70 $hr^{-1}$.

COMPARATIVE EXAMPLE 1

Preparation of a Solid Catalyst

The same solid catalyst preparation procedures as in Example 1 were carried out except that 0.33 g of palladium chloride ($PdCl_2$), 0.64 g of cupric chloride ($CuCl_2 \cdot 2H_2O$) and 0.679 g of ammonium molybdate

[(NH₄)₆Mo₇O₂₄·4H₂O] were heat-dissolved in 70 ml of an aqueous solution of 25% by weight of ammonia at a temperature of 80° C. to 90° C.

The empirical composition of the resultant solid catalyst was $PdCl_2\text{-}CuCl_2\text{-}(NH_4)_6Mo_7O_{24}/C$ (activated carbon). In this solid catalyst, the content of the first catalyst component in terms of palladium was 1% based on the weight of the activated carbon carrier and the atom equivalent ratio of the metals (Pd, Cu and Mo) was Pd : Cu : Mo = 1 : 2.0 : 2.1.

Production of Dimethyl Carbonate

The same dimethyl carbonate production procedures as in Example 1 were carried out except that the above-mentioned catalyst was used in place of the catalyst of Example 1.

In the gas chromatographic analyst, it was confirmed that the STY of dimethyl carbonate was 402 g/l·hr at 2 hours after the start of the reaction procedure and 381 g/l at 7 hours after the start of the reaction procedure, and the catalytic activity reduction coefficient of the catalyst Da was 1.10 hr⁻¹.

EXAMPLES 2 to 10

In each of Examples 2 to 10, the same procedures as in Example 1 were carried out except that the catalyst had the empirical composition as shown in Table 1 and the gram atom equivalent ratio of the metals in the catalyst was as shown in Table 1.

Namely, the first catalyst component consisted of $PdCl_2$, $PdSO_4$, or $RuCl_4$; the second catalyst component consisted of $CuCl_2$, $FeCl_3$, $BiCl_3$, $CuSO_4$, $CoCl_2$ or $SnCl_4$; the third catalyst component consisted of $(NH_4)_6Mo_7O_{24}$, $VOSO_4$, $NH_4VO_3$, or $(NH_4)_{10}HW_{12}O_{46}$; the fourth catalyst component consisted of KF, NaF, LiF, and the solid carrier consisted of activated carbon, $TiO_2$, or diatomaceous earth, as indicated in Table 1.

In the production of dimethyl carbonate, the initial STY of the dimethyl carbonate at 2 hours after the start of the reaction procedure, and the catalytic activity reduction coefficient of the catalyst, were as shown in Table 1.

COMPARATIVE EXAMPLES 2 to 8

In each of Comparative Examples 2 to 8, the same procedures as in Example 1 were carried out except that the catalyst had the empirical composition as shown in Table 1 and the gram atom equivalent ratio of the metals in the catalyst was as shown in Table 1.

Namely, the first catalyst component consisted of $PdCl_2$, $PdSO_4$, or $RuCl_4$; the second catalyst component consisted of $CuCl_2$, $FeCl_3$, $BiCl_3$, $CuSO_4$, $CoCl_2$ or $SnCl_4$; the third catalyst component consisted of $(NH_4)_6Mo_7O_{24}$, $VOSO_4$, or $NH_4VO_3$; the fourth catalyst component was not employed, and the solid carrier consisted of activated carbon, $TiO_2$, or diatomaceous earth, as indicated in Table 1.

In the production of dimethyl carbonate, the initial STY of the dimethyl carbonate at 2 hours after the start of the reaction procedure, and the catalytic activity reduction coefficient of the catalyst, were as shown in Table 1.

TABLE 1

| Example No. | | Empirical composition of catalyst | Gram atom equivalent ratio of metals in catalyst | Initial STY(*) Yo (g/l · hr) | Catalytic activity reduction coefficient Da (hr⁻¹) |
|---|---|---|---|---|---|
| Example | 2 | $PdCl_2$—$CuCl_2$—$(NH_4)_6Mo_7O_{24}$—KF/C | Pd/Cu/Mo/F = 1:2:2.1:1 | 450 | 0.40 |
| | 3 | $PdCl_2$—$CuCl_2$—$(NH_4)_6Mo_7O_{24}$—NaF/C | Pd/Cu/Mo/F = 1:2:2.1:2 | 470 | 0.60 |
| | 4 | $PdCl_2$—$CuCl_2$—$(NH_4)_6Mo_7O_{24}$—LiF/C | Pd/Cu/Mo/F = 1:2:2.1:2 | 480 | 0.70 |
| | 5 | $PdCl_2$—$FeCl_3$—$VOSO_4$—KF/$TiO_2$ | Pd/Fe/V/F = 1:1:1:2 | 395 | 1.10 |
| | 6 | $PdCl_2$—$BiCl_3$—$(NH_4)_6Mo_7O_{24}$—KF/C | Pd/Bi/Mo/F = 1:5:3:2 | 363 | 0.37 |
| | 7 | $PdCl_2$—$CuCl_2$—$NH_4VO_3$—KF/C | Pd/Cu/V/F = 1:2:1:1 | 440 | 0.90 |
| | 8 | $PdCl_2$—$CuSO_4$—$(NH_4)_{10}HW_{12}O_{46}$—KF/C | Pd/Cu/W/F = 1:2:1:1 | 383 | 0.70 |
| | 9 | $PdSO_4$—$CoCl_2$—$NH_4VO_3$—KF/Diatomaceous earth | Pd/Co/V/F = 1:2:1:1 | 333 | 0.40 |
| | 10 | $RuCl_4$—$SnCl_4$—$NH_4VO_3$—KF/C | Ru/Sn/V/F = 1:2:1:2 | 260 | 1.60 |
| Comparative Example | 2 | $PdCl_2$—$FeCl_3$—$VOSO_4$—$TiO_2$ | Pd/Fe/V = 1:1:1 | 383 | 1.20 |
| | 3 | $PdCl_2$—$BiCl_3$—$(NH_4)_6Mo_7O_{24}$/C | Pd/Bi/Mo = 1:5:3 | 352 | 0.40 |
| | 4 | $PdCl_2$—$CuCl_2$—$NH_4VO_3$/C | Pd/Cu/V = 1:2:1 | 430 | 1.00 |
| | 5 | $PdCl_2$—$CuSO_4$—$(NH_4)_{10}HW_{12}O_{46}$/C | Pd/Cu/W = 1:2:1 | 375 | 0.80 |
| | 6 | $PdSO_4$—$CoCl_2$—$NH_4VO_3$-/Diatomaceous earth | Pd/Co/V = 1:2:1 | 325 | 0.50 |
| | 7 | $RuCl_4$—$SnCl_4$—$NH_4VO_3$/C | Ru/Sn/V = 1:2:1 | 253 | 1.80 |
| | 8 | $PdCl_2$—$CuCl_2$—$(NH_4)_6Mo_7O_{24}$—KF/C | Pd/Cu/Mo/F = 1:2:2.1:25 | 120 | 5.50 |

Note: (*) . . . Space time yield in g/l · hr of dimethyl carbonate 2 hours after start of reaction procedure

EXAMPLE 11

The same procedures as in Example 1 were carried out except that the reaction temperature was changed from 120° C. to 100° C.

The initial STY(Yo) of dimethyl carbonate at 2 hours after the start of the reaction procedure was 290 g/l·hr and the catalytic activity reduction coefficient Da was 0.09 hr⁻¹.

EXAMPLE 12

The same procedures as in Example 1 were carried out except that the reaction temperature was changed from 120° C. to 140° C.

The initial STY(Yo) of dimethyl carbonate at 2 hours after the start of the reaction procedure was 735 g/l·hr and the catalytic activity reduction coefficient Da was 1.90 hr⁻¹.

EXAMPLE 13

The same procedures as in Example 1 were carried out except that in the mixed gas fed to the reaction tube, the methyl nitrite was replaced by ethyl nitrite and methyl alcohol was replaced by ethyl alcohol.

The initial STY(Yo) of dimethyl carbonate at 2 hours after the start of the reaction procedure was 534 g/l·hr and the catalytic activity reduction coefficient Da was 1.10 hr$^{-1}$.

EXAMPLE 14

The same procedures as in Example 1 were carried out except that the solid catalyst was placed in an amount of 8.5 ml in the reaction tube, and in the reaction procedure, a mixed gas consisting of 9% by volume of methyl nitrite, 9% by volume of carbon monoxide, 4% by volume of nitrogen monoxide, 3% by volume of methyl alcohol and 75% by volume of nitrogen was fed to the reaction tube through a top end thereof at a space velocity (GHSV) of 2500 hr$^{-1}$, and the reaction was carried out under a pressure of 2.0 kg/cm$^2$G.

The STY of dimethyl carbonate was 275 g/l·hr at 2 hours after the start of the reaction procedure and 275 g/l·hr at 22 hours after the start of the reaction procedure, and thus the catalytic activity of the catalyst was not reduced within the reaction time of at least 22 hours.

EXAMPLE 15

Preparation of Catalyst

A catalyst component aqueous solution containing Pd, Cu, Mo and potassium acetate was prepared by heat-dissolving 0.33 g of palladium chloride (PdCl$_2$), 0.641 g of cupric chloride (CuCl$_2$·2H$_2$O), 0.679 g of ammonium molybdate [(NH$_4$)$_6$Mo$_7$O$_{24}$√4H$_2$O] and 0.365 g of potassium acetate in 70 ml of an aqueous solution of 25% by weight of ammonia at a temperature of 80° C. to 90° C.

Separately, 20 g of particulate activated carbon (c) having a size of 0.5 to 0.7 mm was immersed and dispersed in 50 ml of an aqueous solution of 25% by weight of ammonia, then the above-mentioned catalyst component solution was mixed with the activated carbon dispersion. The resultant mixture was left to stand for one hour.

The mixture was then subjected to water evaporation at a temperature of 80° C. under a reduced pressure, and dried in a nitrogen gas atmosphere at a temperature of 200° C. to provide a solid catalyst.

The resultant solid catalyst had an empirical composition of PdCl$_2$-CuCl$_2$-(NH$_4$)$_6$Mo$_7$O$_{24}$-CH$_3$COOK/C (activated carbon).

The first catalyst component was present in an amount in terms of metallic palladium of 1% based on the weight of the solid carrier consisting of the activated carbon.

The content ratio in atom equivalent of the first, second, third and fourth catalyst components were Pd : Cu : Mo : K = 1 : 2 : 2.1 : 2.

Production of a Carbonic Acid Diester

The above-mentioned solid catalyst in an amount of 2.5 ml was placed in a gas phase reaction tube having an inside diameter of 20 mm and equipped with an outside heating jacket. The reaction tube filled by the solid catalyst was fixed vertically and a heating medium consisting of a silicone oil was made to flow through the outside heating jacket to maintain the inside temperature of the reaction tube at a level of 120° C.

A mixed gas consisting of 8% by volume of methyl nitrite, 8% by volume of carbon monoxide, 3% by volume of nitrogen monoxide, 10% by volume of methyl alcohol and 71% by volume of nitrogen was fed into the reaction tube through a top end thereof at a space velocity (GHSV) of 8500 hr$^{-1}$ under the ambient atmospheric pressure. The methyl nitrite was produced from nitrogen monoxide, oxygen and methyl alcohol.

In the reaction tube, the methyl nitrite reacted with carbon monoxide in the presence of the solid catalyst.

The resultant reaction mixture discharged from the reaction tube through a bottom thereof was made to flow through methyl alcohol cooled with ice, to collect the resultant reaction product. The collected reaction product was subjected to gas chromatography, and it was confirmed that at 2 hours after the start of the reaction procedure, the space time yield (STY) of dimethyl carbonate was 443 g/l·hr, and at 8 hours after the start of the reaction procedure, the STY of dimethyl carbonate was 443 g/l·hr. Thus, the solid catalyst exhibited a catalytic activity reduction coefficient Da of 0.40 hr$^{-1}$.

COMPARATIVE EXAMPLE 9

Preparation of a Solid Catalyst

The same solid catalyst preparation procedures as in Example 15 were carried out except that 0.33 g of palladium chloride (PdCl$_2$), 0.64 g of cupric chloride (CuCl$_2$·2H$_2$O) and 0.679 g of ammonium molybdate [(NH$_4$)$_6$Mo$_7$O$_{24}$H$_2$O] were heat-dissolved in 70 ml of an aqueous solution of 25% by weight of ammonia at a temperature of 80° C. to 90° C.

The empirical composition of the resultant solid catalyst was PdCl$_2$-CuCl$_2$-(NH$_4$)$_6$Mo$_7$O$_{24}$/C (activated carbon). In this solid catalyst, the content of the first catalyst component in terms of palladium was 1% based on the weight of the activated carbon carrier and the atom equivalent ratio of the metals (Pd, Cu and Mo) was Pd : Cu : Mo = 1 : 2.0 : 2.1.

Production of Dimethyl Carbonate

The same dimethyl carbonate production procedures as in Example 1 were carried out except that the above-mentioned catalyst was used in place of the catalyst of Example 1.

In the gas chromatographic analyst, it was confirmed that the STY of dimethyl carbonate was 402 g/l·hr at 2 hours after the start of the reaction procedure and 381 g/l at 7 hours after the start of the reaction procedure, and the catalytic activity reduction coefficient of the catalyst Da was 1.10 hr$^{-1}$.

EXAMPLES 16 to 25

In each of Examples 16 to 25, the same procedures as in Example 15 were carried out except that the catalyst had the empirical composition as shown in Table 2 and the gram atom equivalent ratio of the metals in the catalyst was as shown in Table 2.

Namely, the first catalyst component consisted of PdCl$_2$, PdSO$_4$, or RuCl$_4$; the second catalyst component consisted of CuCl$_2$, FeCl$_3$, BiCl$_3$, CuSO$_4$, CoCl$_2$ or SnCl$_4$; the third catalyst component consisted of (NH$_4$)$_6$Mo$_7$O$_{24}$, VOSO$_4$, NH$_4$VO$_3$, or (NH$_4$)$_{10}$HW$_{12}$O$_{46}$; the fourth catalyst component consisted of CH$_3$COONa, HCOOK, (CH$_3$COO)$_2$Ca, (HCOO)$_2$Ba, or CH$_3$COOK, and the solid carrier consisted of activated carbon, TiO$_2$, or diatomaceous earth, as indicated in Table 2.

In the production of dimethyl carbonate, the initial STY of the dimethyl carbonate at 2 hours after the start of the reaction procedure, and the catalytic activity reduction coefficient of the catalyst, were as shown in Table 2.

COMPARATIVE EXAMPLES 10 to 15

In each of Comparative Examples 10 to 15, the same procedures as in Example 15 were carried out except that the catalyst had the empirical composition as shown in Table 2 and the gram atom equivalent ratio of the metals in the catalyst was as shown in Table 2.

Namely, the first catalyst component consisted of $PdCl_2$, $PdSO_4$, or $RuCl_4$; the second catalyst component consisted of $CuCl_2$, $FeCl_3$, $BiCl_3$, $CuSO_4$, $CoCl_2$ or $SnCl_4$; the third catalyst component consisted of $(NH_4)_6Mo_7O_{24}$, $VOSO_4$, or $NH_4VO_3$, or $(NH_4)_{10}HW_{12}O_{46}$; the fourth catalyst component was not employed, and the solid carrier consisted of activated carbon, $TiO_2$, or diatomaceous earth, as indicated in Table 2.

In the production of dimethyl carbonate, the initial STY of the dimethyl carbonate at 2 hours after the start of the reaction procedure, and the catalytic activity reduction coefficient of the catalyst, were as shown in Table 2.

the methyl nitrite was replaced by ethyl nitrite and methyl alcohol was replaced by ethyl alcohol.

The initial STY(Yo) of dimethyl carbonate at 2 hours after the start of the reaction procedure was 443 g/l·hr and the catalytic activity reduction coefficient Da was 0.52 $hr^{-1}$.

EXAMPLE 29

The same procedures as in Example 15 were carried out except that the solid catalyst was placed in an amount of 5.0 ml in the reaction tube, and in the reaction procedure, a mixed gas consisting of 9% by volume of methyl nitrite, 9% by volume of carbon monoxide, 4% by volume of nitrogen monoxide, 3% by volume of methyl alcohol and 75% by volume of nitrogen was fed to the reaction tube through a top end thereof at a space velocity (GHSV) of 4000 $hr^{-1}$, and the reaction was carried out under a pressure of 2.0 $kg/cm^2G$.

The STY of dimethyl carbonate was 514 g/l·hr at 2 hours after the start of the reaction procedure and 514 g/l·hr at 22 hours after the start of the reaction procedure, and thus the catalytic activity of the catalyst was not reduced within the reaction time of at least 22 hours.

TABLE 2

| Example No. | | Empirical composition of catalyst | Gram atom equivalent ratio of metals in catalyst | Initial STY(*) Yo (g/l · hr) | Catalytic activity reduction coefficient Da ($hr^{-1}$) |
|---|---|---|---|---|---|
| Example | 16 | $PdCl_2$—$CuCl_2$—$(NH_4)_6Mo_7O_{24}$—$CH_3COONa/C$ | Pd/Cu/Mo/Na = 1:2:2.1:1 | 420 | 0.63 |
| | 17 | $PdCl_2$—$CuCl_2$—$(NH_4)_6Mo_7O_{24}$—HCOOK/C | Pd/Cu/Mo/K = 1:2:2.1:2 | 390 | 0.59 |
| | 18 | $PdCl_2$—$CuCl_2$—$(NH_4)_6Mo_7O_{24}$—$(CH_3COO)_2Ca/C$ | Pd/Cu/Mo/Ca = 1:2:2.1:2 | 407 | 0.61 |
| | 19 | $PdCl_2$—$CuCl_2$—$(NH_4)_6Mo_7O_{24}$—$(HCOO)_2Ba/C$ | Pd/Cu/Mo/Ba = 1:2:2.1:2 | 394 | 0.55 |
| | 20 | $PdCl_2$—$FeCl_3$—$VOSO_4$—$CH_3COOK/TiO_2$ | Pd/Fe/V/K = 1:1:1:2 | 395 | 0.82 |
| | 21 | $PdCl_2$—$BiCl_3$—$(NH_4)_6Mo_7O_{24}$—$CH_3COOK/C$ | Pd/Bi/Mo/K = 1:5:3:2 | 380 | 0.27 |
| | 22 | $PdCl_2$—$CuCl_2$—$NH_4VO_3$—$CH_3COOK/C$ | Pd/Cu/V/K = 1:2:1:1 | 412 | 0.62 |
| | 23 | $PdCl_2$—$CuSO_4$—$(NH_4)_{10}HW_{12}O_{46}$—$CH_3COOK/C$ | Pd/Cu/W/K = 1:2:1:1 | 370 | 0.53 |
| | 24 | $PdSO_4$—$CoCl_2$—$NH_4VO_3$—$CH_3COOK/$Diatomaceous earth | Pd/Co/V/K = 1:2:1:1 | 320 | 0.33 |
| | 25 | $RuCl_4$—$SnCl_4$—$NH_4VO_3$—$CH_3COOK/C$ | Ru/Sn/V/F = 1:2:1:2 | 295 | 1.10 |
| Comparative Example | 10 | $PdCl_2$—$FeCl_3$—$VOSO_4/TiO_2$ | Pd/Fe/V = 1:1:1 | 388 | 1.18 |
| | 11 | $PdCl_2$—$BiCl_3$—$(NH_4)_6Mo_7O_{24}/C$ | Pd/Bi/Mo = 1:5:3 | 357 | 0.38 |
| | 12 | $PdCl_2$—$CuCl_2$—$NH_4VO_3/C$ | Pd/Cu/V = 1:2:1 | 435 | 0.99 |
| | 13 | $PdCl_2$—$CuSO_4$—$(NH_4)_{10}HW_{12}O_{46}/C$ | Pd/Cu/W = 1:2:1 | 380 | 0.77 |
| | 14 | $PdSO_4$—$CoCl_2$—$NH_4VO_3/$Diatomaceous earth | Pd/Co/V = 1:2:1 | 330 | 0.51 |
| | 15 | $RuCl_4$—$SnCl_4$—$NH_4VO_3/C$ | Ru/Sn/V = 1:2:1 | 258 | 1.78 |

Note: (*) ... Space time yield in g/l · hr of dimethyl carbonate 2 hours after start of reaction procedure

EXAMPLE 26

The same procedures as in Example 15 were carried out except that the reaction temperature was changed from 120° C. to 100° C.

The initial STY(Yo) of dimethyl carbonate at 2 hours after the start of the reaction procedure was 260 g/l·hr and the catalytic activity reduction coefficient Da was 0.08 $hr^{-1}$.

EXAMPLE 27

The same procedures as in Example 1 were carried out except that the reaction temperature was changed from 120° C. to 140° C.

The initial STY(Yo) of dimethyl carbonate at 2 hours after the start of the reaction procedure was 550 g/l·hr and the catalytic activity reduction coefficient Da was 1.21 $hr^{-1}$.

EXAMPLE 28

The same procedures as in Example 15 were carried out except that in the mixed gas fed to the reaction tube,

EXAMPLE 30

Preparation of Catalyst

A catalyst component aqueous solution containing Pd, Cu, Mo and patassium chloride was prepared by heat-dissolving 0.33 g of palladium chloride ($PdCl_2$), 0.641 g of cupric chloride ($CuCl_2\cdot 2H_2O$), 0.679 g of ammonium molybdate [$(NH_4)_6MO_7O_{24}\cdot 4H_2O$] and 0.227 g of potassium chloride in 70 ml of an aqueous solution of 25% by weight of ammonia at a temperature of 80° C. to 90° C.

Separately, 20 g of particulate activated carbon (C) having a size of 0.5 to 0.7 mm was immersed and dispersed in 50 ml of an aqueous solution of 25% by weight of ammonia then the above-mentioned catalyst component solution was mixed with the activated carbon dispersion. The resultant mixture was left to stand for one hour.

The mixture was then subjected to water evaporation at a temperature of 80° under a reduced pressure and dried in a nitrogen gas atmosphere at a temperature of 200° C. to provide a solid catalyst.

The resultant solid catalyst had an empirical composition of $PdCl_2\text{-}CuCl_2\text{-}(NH_4)_6Mo_7O_{24}\text{-}KCl/C$ (activated carbon).

The first catalyst component was present in an amount in terms of metallic palladium of 1% based on the weight of the solid carrier consisting of the activated carbon.

The content ratio in atom equivalent of the first, second, third and fourth catalyst components were Pd : Cu : Mo : K = 1 : 2 : 2.1 : 2

Production of a Carbonic Acid Diester

The above-mentioned solid catalyst in an amount of 2.5 ml was placed in a gas phase reaction tube having an inside diameter of 20 mm and equipped with an outside heating jacket. The reaction tube filled by the solid catalyst was fixed vertically and a heating medium consisting of a silicone oil was made to flow through the outside heating jacket to maintain the inside temperature of the reaction tube at a level of 120° C.

A mixed gas consisting of 8% by volume of methyl nitrite, 8% by volume of carbon monoxide, 3% by volume of nitrogen monoxide, 10% by volume of methyl alcohol and 71% by volume of nitrogen was fed into the reaction tube through a top and thereof at a space velocity (GHSV) of 8500 $hr^{-1}$ under the ambient atmosphere pressure. The methyl nitrite was produced from nitrogen monoxide, oxygen and methyl alcohol.

In the reaction tube, the methyl nitrite reacted with carbon monoxide in the presence of the solid catalyst.

The resultant reaction mixture discharged from the reaction tube through a bottom thereof was made to flow through methyl alcohol cooled with ice to collect the resultant reaction product. The collected reaction product was subjected to gas chromatography, and it was confirmed that, at 2 hours after the start of the reaction procedure, the space time yield (STY) of dimethyl carbonate was 405 g/l·hr, and at 8 hours after the start of the reaction procedure, the STY of dimethyl carbonate was 402 g/l·hr. Thus, the solid catalyst exhibited a catalytic activity reduction coefficient Da of 0.13 $hr^{-1}$.

EXAMPLE 31 to 41

In each of Examples 31 to 41, the same procedures as in Example 30 were carried out except that the catalyst had the empirical composition as shown in Table 3 and the gram atom equivalent ratio of the metals in the catalyst was as shown in Table 3.

Namely, the first catalyst component consisted of $PdCl_2$, $PdSO_4$, or $RuCl_4$; the second catalyst component consisted of $CuCl_2$, $FeCl_3$, $BiCl_3$, $CuSO_4$, $CoCl_2$ or $SnCl_4$; the third catalyst component consisted of $(NH_4)_6Mo_7O_{24}$, $VOSO_4$, $NH_4VO_3$, or $(NH_4)_{10}HW_{12}O_{46}$; the fourth catalyst component consisted of KCl, LiCl, NaCl, RbCl or CsCl and the solid carrier consisted of activated carbon, $TiO_2$, or diatomaceous earth, as indicated in Table 1.

In the production of dimethyl carbonae, the initial STY of the dimethyl carbonate at 2 hours after the start of the reaction procedure, and the catalytic activity reduction coefficient of the catalyst were as shown in Table 3.

COMPARATIVE EXAMPLES 16 to 21

In each of Comparative Examples 16 to 21, the same procedures as in Example 30 were carried out except that the catalyst had the empirical composition as shown in Table 3 and the gram atom equivalent ratio of the metals in the catalyst was as shown in Table 3.

Namely, the first catalyst component consisted of $PdCl_2$, $PdSO_4$, or $RuCl_4$; the second catalyst component consisted of $CuCl_2$, $FeCl_3$, $BiCl_3$, $CuSO_4$, $CoCl_2$ or $SnCl_4$; the third catalyst component consisted of $(NH_4)_6Mo_7O_{24}$, $VOSO_4$, or $NH_4VO_3$, or $(NH_4)_{10}HW_{12}O_{46}$;, the fourth catalyst component was not employed, and the solid carrier consisted of activated carbon, $TiO_2$, or diatomaceous earth, as indicated in Table 1.

In the production of dimethyl carbonate the initial STY of the dimethyl carbonate at 2 hours after the start of the reaction procedure, and the catalytic activity reduction coefficient of the catalyst were as shown in Table 3.

TABLE 3

| Example No. | | Empirical composition of catalyst | Gram atom equivalent ratio of metals in catalyst | Initial STY(*) Yo (g/l · hr) | Catalytic activity reduction coefficient Da ($hr^{-1}$) |
| --- | --- | --- | --- | --- | --- |
| Example | 31 | $PdCl_2$—$CuCl_2$—$(NH_4)_6Mo_7O_{24}$—KCl/C | Pd/Cu/Mo/K = 1:2:2.1:1 | 420 | 0.66 |
| | 32 | $PdCl_2$—$CuCl_2$—$(NH_4)_6Mo_7O_{24}$—LiCl/C | Pd/Cu/Mo/Li = 1:2:2.1:2 | 418 | 0.87 |
| | 33 | $PdCl_2$—$CuCl_2$—$(NH_4)_6Mo_7O_{24}$—NaCl/C | Pd/Cu/Mo/Na = 1:2:2.1:2 | 407 | 0.54 |
| | 34 | $PdCl_2$—$CuCl_2$—$(NH_4)_6Mo_7O_{24}$—RbCl/C | Pd/Cu/Mo/Rb = 1:2:2.1:2 | 415 | 0.15 |
| | 35 | $PdCl_2$—$CuCl_2$—$(NH_4)_6Mo_7O_{24}$—CsCl/C | Pd/Cu/Mo/Cs = 1:2:2.1:2 | 413 | 0.14 |
| | 36 | $PdCl_2$—$FeCl_3$—$VOSO_4$—KCl/$TiO_2$ | Pd/Fe/V/K = 1:1:1:2 | 350 | 0.70 |
| | 37 | $PdCl_2$—$BiCl_3$—$(NH_4)_6Mo_7O_{24}$—KCl/C | Pd/Bi/Mo/K = 1:5:3:2 | 358 | 0.30 |
| | 38 | $PdCl_2$—$CuCl_2$—$NH_4VO_3$—KCl/C | Pd/Cu/V/K = 1:2:1:1 | 375 | 0.78 |
| | 39 | $PdCl_2$—$CuSO_4$—$(NH_4)_{10}HW_{12}O_{46}$—KCl/C | Pd/Cu/W/K = 1:2:1:1 | 340 | 0.55 |
| | 40 | $PdSO_4$—$CoCl_2NH_4VO_3$—KCl/Diatomaceous earth | Pd/Co/V/K = 1:2:1:1 | 307 | 0.36 |
| | 41 | $RuCl_4$—$SnCl_4$—$NH_4VO_3$—KCl/C | Ru/Sn/V/K = 1:2:1:2 | 270 | 1.15 |
| Comparative Example | 16 | $PdCl_2$—$FeCl_3$—$VOSO_4$/$TiO_2$ | Pd/Fe/V = 1:1:1 | 388 | 1.18 |
| | 17 | $PdCl_2$—$BiCl_3$—$(NH_4)_6Mo_7O_{24}$/C | Pd/Bi/Mo = 1:5:3 | 357 | 0.38 |
| | 18 | $PdCl_2$—$CuCl_2$—$NH_4VO_3$/C | Pd/Cu/V = 1:2:1 | 435 | 0.99 |
| | 19 | $PdCl_2$—$CuSO_4$—$(NH_4)_{10}HW_{12}O_{46}$/C | Pd/Cu/W = 1:2:1 | 380 | 0.77 |
| | 20 | $PdSO_4$—$CoCl_2$—$NH_4VO_3$/Diatomaceous earth | Pd/Co/V = 1:2:1 | 330 | 0.51 |
| | 21 | $RuCl_4$—$SnCl_4$—$NH_4VO_3$/C | Ru/Sn/V = 1:2:1 | 258 | 1.78 |

Note: (*) . . . Space time yield in g/l · hr of dimethyl carbonate 2 hours after start of reaction procedure

EXAMPLE 42

The same procedures as in Example 30 were carried out except that the reaction temperature was changed from 120° C. to 100° C.

The initial STY(Yo) of dimethyl carbonate at 2 hours after the start of the reaction procedure was 243 g/l·hr and the catalytic activity reduction coefficient Da was 0.10 hr$^{-1}$.

EXAMPLE 43

The same procedures as in Example 30 were carried out except that the reaction temperature was changed from 120° C. to 140° C.

The initial STY(Yo) of dimethyl carbonate at 2 hours after the start of the reaction procedure was 607 g/l·hr and the catalytic activity reduction coefficient Da was 0.92 hr$^{-1}$.

EXAMPLE 13

The same procedures as in Example 30 were carried out except that in the mixed gas fed to the reaction tube, the methyl nitrite was replaced by ethyl nitrite and methyl alcohol was replaced by ethyl alcohol.

The initial STY(Yo) of dimethyl carbonate at 2 hours after the start of the reaction procedure was 413 g/l·hr and the catalytic activity reduction coefficient Da was 0.34 hr$^{-1}$.

EXAMPLE 46

The same procedures as in Example 1 were carried out except that the solid catalyst was placed in an amount of 5.0 ml in the reaction tube, and in the reaction procedure, a mixed gas consisting of 9% by volume of methyl nitrite, 9% by volume of carbon monoxide, 4% by volume of nitrogen monoxide, 3% by volume of methyl alcohol and 75% by volume of nitrogen was fed to the reaction tube through stop end thereof at a space velocity (GHSV) of 4000 hr$^{-1}$, and the reaction was carried out under a pressure of 2.0 kg/cm$^2$G.

The STY dimethyl carbonate was 440 g/l·hr at 2 hours after the start of the reaction procedure, and 440 g/l·hr at 22 hours after the start of the reaction procedure, and thus the catalytic activity of the catalyst was not reduced within the reaction time of at least 22 hours.

EXAMPLE 47

Preparation of Catalyst

A catalyst component aqueous solution containing Pd, Cu, Mo and potassium dihydrogen phosphate was prepared by heat-dissolving 0.33 g of palladium chloride (PdCl$_2$), 0.641 g of cupric chloride (CuCl$_2$·2H$_2$O), 0.679 g of ammonium molybdate [(NH$_4$)$_6$Mo$_7$O$_{24}$·4H$_2$O] and 0.506 g of potassium dihydrogen phosphate in 70 ml of an aqueous solution of 25% by weight of ammonia at a temperature of 80° C. to 90° C.

Separately, 20 g particulate activated carbon (C) having a size of 0.5 to 0.7 mm was immersed and dispersed in 50 ml of an aqueous solution of 25% by weight of ammonia then the above-mentioned catalyst component solution was mixed with the activated carbon dispersion. The resultant mixture was left to stand for one hour.

The mixture was then subjected to water evaporation at a temperature of 80° C. under a reduced pressure and dried in a nitrogen gas atmosphere at a temperature of 200° C. to provide a solid catalyst.

The resultant solid catalyst had an empirical composition of PdCl$_2$-CuCl$_2$-(NH$_4$)$_6$Mo$_7$O$_{24}$-KH$_2$PO$_4$/C (activated carbon).

The first catalyst component was present in an amount in terms of metallic palladium of 1% based on the weight of the solid carrier consisting of the activated carbon.

The content ratio in atom equivalent of the first, second, third and fourth catalyst components were Pd : Cu : Mo : KF = 1 : 2 : 2.1 : 2

Production of a Carbonic Acid Diester

The above-mentioned solid catalyst in an amount of 2.5 ml was placed in a gas phase reaction tube having an inside diameter of 20 mm and equipped with an outside heating jacket. The reaction tube filled by the solid catalyst was fixed vertically and a heating medium consisting of a silicone oil was made to flow through the outside heating jacket to maintain the inside temperature of the reaction tube at a level of 120° C.

A mixed gas consisting of 8% by volume of methyl nitrite, 8% by volume of carbon monoxide, 3% by volume of nitrogen monoxide, 10% by volume of methyl alcohol and 71% by volume of nitrogen was fed into the reaction tube through a top end thereof at a space velocity (GHSV) of 8500 hr$^{-1}$ under the ambient atmosphere pressure. The methyl nitrite was produced from nitrogen monoxide, oxygen and methyl alcohol.

In the reaction tube, the methyl nitrite reacted with carbon monoxide in the pressure of the solid catalyst.

The resultant reaction mixture discharged from the reaction tube through a bottom thereof was made to flow through methyl alcohol cooled with ice, to collect the resultant reaction product. The collected reaction product was subjected to a gas chromatography, and it was confirmed that, at 2 hours after the start of the reaction procedure, the space time yield (STY) of dimethyl carbonate was 515 g/l·hr, and at 9 hours after the start of the reaction procedure, the STY of dimethyl carbonate was 494 g/l·hr. Thus, the solid catalyst exhibited a catalytic activity reduction coefficient Da of 0.65 hr$^{-1}$.

EXAMPLE 48 to 58

In each of Examples 48 to 58, the same procedures as in Example 47 were carried out except that the catalyst had the empirical composition as shown in Table 4 and the gram atom equivalent ratio of the metals in the catalyst was as shown in Table 4.

Namely, the first catalyst component consisted of PdCl$_2$, PdSO$_4$, or RuCl$_4$; the second catalyst component consisted of CuCl$_2$, FeCl$_3$, BiCl$_3$, CuSO$_4$, CoCl$_2$ or SnCl$_4$; the third catalyst component consisted of (NH$_4$)$_6$Mo$_7$O$_{24}$, VOSO$_4$, or NH$_4$VO$_3$; the fourth catalyst component consisted of NaH$_2$PO$_4$, K$_2$HPO$_4$, Na$_3$PO$_4$, Ca(H$_2$PO$_4$)$_2$, SrHPO$_4$, K$_2$HPO$_4$, or KH$_2$PO$_4$, and the solid carrier consisted of activated carbon, TiO$_2$, or diatomaceous earth, as indicated in Table 4.

In the production of dimethyl carbonate the initial STY of the dimethyl carbonate at 2 hours after the start of the reaction procedure, and the catalytic activity reduction coefficient of the catalyst were as shown in Table 4.

COMPARATIVE EXAMPLES 23 to 28

In each of Comparative Examples 23 to 28, the same procedures as in Example 47 were carried out except that the catalyst had the empirical composition as shown in Table 4 and the gram atom equivalent ratio of the metals in the catalyst was as shown in Table 4.

Namely, the first catalyst component consisted of $PdCl_2$, $PdSO_4$, or $RuCL_4$; the second catalyst component consisted of $CuCl_2$, $FeCl_3$, $BiCl_3$, $CuSO_4$, $CoCl_2$ or $SnCl_4$; the third catalyst component consisted of $(NH_4)_6Mo_7O_{24}$, $VOSO_4$, $NH_4VO_3$ or $(NH_4)_{10}HW_{12}O_{46}$; the fourth catalyst component was not employed, and the solid carrier consisted of activated carbon, $TiO_2$, or diatomaceous earth, as indicated in Table 4.

In the production of dimethyl carbonate the initial STY of the dimethyl carbonate at 2 hours after the start of the reaction procedure, and the catalytic activity reduction coefficient of the catalyst were as shown in Table 4.

EXAMPLE 62

The same procedures as in Example 47 were carried out except that the solid catalyst was placed in an amount of 5.0 ml in the reaction tube, and in the reaction procedure, a mixed gas consisting of 9% by volume of methyl nitrite, 9% by volume of carbon monoxide, 4% by volume of nitrogen monoxide, 3% by volume of methyl alcohol and 75% by volume of nitrogen was fed to the reaction tube through a top end thereof at a space velocity (GHSV) of 4000 $hr^{-1}$ and the reaction was carried out under a pressure of 2.0 $kg/cm^2G$.

The STY of dimethyl carbonate was 480 g/l·hr at 2 hours after the start of the reaction procedure and 480 g/l·hr at 22 hours after the start of the reaction procedure, and thus the catalytic activity of the catalyst was

TABLE 4

| Example No. | | Empirical composition of catalyst | Gram atom equivalent ratio of metals in catalyst | Initial STY(*) Yo (g/l · hr) | Catalytic activity reduction coefficient Da ($hr^{-1}$) |
|---|---|---|---|---|---|
| Example | 48 | $PdCl_2$—$CuCl_2$—$(NH_4)_6Mo_7O_{24}$—$NaH_2PO_4$/C | Pd/Cu/Mo/Na = 1:2:2.1:2 | 396 | 0.71 |
| | 49 | $PdCl_2$—$CuCl_2$—$(NH_4)_6Mo_7O_{24}$—$K_2HPO_4$/C | Pd/Cu/Mo/K = 1:2:2.1:2 | 405 | 0.62 |
| | 50 | $PdCl_2$—$CuCl_2$—$(NH_4)_6Mo_7O_{24}$—$Na_3PO_4$/C | Pd/Cu/Mo/Na = 1:2:2.1:3 | 385 | 0.54 |
| | 51 | $PdCl_2$—$CuCl_2$—$(NH_4)_6Mo_7O_{24}$—$Ca(H_2PO_4)_2$/C | Pd/Cu/Mo/Ca = 1:2:2.1:2 | 383 | 0.71 |
| | 52 | $PdCl_2$—$CuCl_2$—$(NH_4)_6Mo_7O_{24}$—$SrHPO_4$/C | Pd/Cu/Mo/Sr = 1:2:2.1:2 | 390 | 0.55 |
| | 53 | $PdCl_2$—$FeCl_3$—$VOSO_4$—$K_2HPO_4$/$TiO_2$ | Pd/Cu/V/K = 1:1:1:2 | 368 | 0.75 |
| | 54 | $PdCl_2$—$BiCl_3$—$(NH_4)_6Mo_7O_{24}$—$KH_2PO_4$/C | Pd/Bi/Mo/K = 1:5:3:2 | 337 | 0.29 |
| | 55 | $PdCl_2$—$CuCl_2$—$NH_4VO_3$—$KH_2PO_4$/C | Pd/Cu/V/K = 1:2:1:1 | 397 | 0.70 |
| | 56 | $PdCl_2$—$CuSO_4$—$NH_4VO_3$—$KH_2PO_4$/C | Pd/Cu/W/K = 1:2:1:1 | 353 | 0.58 |
| | 57 | $PdSO_4$—$CoCl_2$—$NH_4VO_3$—$KH_2PO_4$/Diatomaceous earth | Pd/Co/V/K = 1:2:1:1 | 316 | 0.30 |
| | 58 | $RuCl_4$—$SnCl_4$—$NH_4VO_3$—$KH_2PO_4$/C | Ru/Sn/V/K = 1:2:1:2 | 240 | 1.23 |
| Comparative Example | 23 | $PdCl_2$—$FeCl_3$—$VOSO_4$/$TiO_2$ | Pd/Fe/V = 1:1:1 | 388 | 1.18 |
| | 24 | $PdCl_2$—$BiCl_3$—$(NH_4)_6Mo_7O_{24}$/C | Pd/Bi/Mo = 1:5:3 | 357 | 0.38 |
| | 25 | $PdCl_2$—$CuCl_2$—$NH_4VO_3$/C | Pd/Cu/V = 1:2:1 | 435 | 0.99 |
| | 26 | $PdCl_2$—$CuSO_4$—$(NH_4)_{10}HW_{12}O_{46}$/C | Pd/Cu/W = 1:2:1 | 380 | 0.77 |
| | 27 | $PdSO_4$—$CoCl_2$—$NH_4VO_3$/Diatomaceous earth | Pd/Co/V = 1:2:1 | 330 | 0.51 |
| | 28 | $RuCl_4$—$SnCl_4$—$NH_4VO_3$/C | Ru/Sn/V = 1:2:1 | 258 | 1.78 |

Note: (*) . . . Space time yield in g/l · hr of dimethyl carbonate 2 hours after start of reaction procedure

EXAMPLE 59

The same procedures as in Example 47 were carried out except that the reaction temperature was changed from 120° C. to 100° C.

The initial STY(Yo) of dimethyl carbonate at 2 hours after the start of the reaction procedure was 270 g/l·hr and the catalytic activity reduction coefficient Da was 0.08 $hr^{-1}$.

EXAMPLE 60

The same procedures as in Example 47 were carried out except that the reaction temperature was changed from 120° C. and to 140° C.

The initial STY(Yo) of dimethyl carbonate at 2 hours after the start of the reaction procedure was 675 g/l·hr and the catalytic activity reduction coefficient Da was 1.7 $hr^{-1}$.

EXAMPLE 61

The same procedures as in Example 47 were carried out except that in the mixed gas fed to the reaction tube, the methyl nitrite was replaced by ethyl nitrite and methyl alcohol was replaced by ethyl alcohol.

The initial STY(Yo) of dimethyl carbonate at 2 hours after the start of the reaction procedure was 467 g/l·hr and the catalytic activity reduction coefficient Da was 0.76 $hr^{-1}$.

not reduced within the reaction time of at least 22 hours.

EXAMPLE 63

Preparation of Palladium Tetramine Molybdate

Palladium Chloride in an amount of 17.73 g (100 m mole) was dissolved in 400 ml of a 25% ammonia aqueous solution at a temperature of 80° C., to the resultant palladium chloride solution was gradually added a solution prepared by dissolving 17.66 g (100/7 m mole) of ammonium molybdate in 150 ml of a 25% ammonia aqueous solution, and immediately a white precipitate was produced. After completion of the adding procedure, the mixture was left to stand for one hour and then subjected to suction filtration. The filtered product was washed with a small amount of methyl alcohol, and dried at a temperature of 120° C. for 10 hours, and the resultant product, in the form of crystals, was obtained in an amount of 31.3 g at an yield of 89%.

The results of the elemental analysis of the resultant crystals were as follows.
Pd: 30.4%, Mo: 27.0%, 0: 23%
N : 15.9%, H : 4.2%
The calculated amounts of elements of $Pd(NH_3)_4MoO_4 \cdot H_2O$ were as follows:
Pd: 30.2%, Mo: 27.2%, 0: 22.7%
N : 15.9%, H : 3.97%

The melting point of the resultant product was measured, and as a result it was found that the crystals were gradually decolored at a temperature of about 160° C. or more, and were decomposed at a temperature of about 180° C. or more.

The crystals were insoluble or very poorly soluble when heated or cooled in petroleum ether, petroleum benzine, n-hexane, ligroin, benzene, toluene, chloroform, carbon tetrachloride, vinyl chloride, carbon disulfide, ethyl acetate, acetonitrile, methyl alcohol, ethyl alcohol, n-butyl alcohol, isopropyl alcohol and cyclohexyl alcohol.

Figure 1:
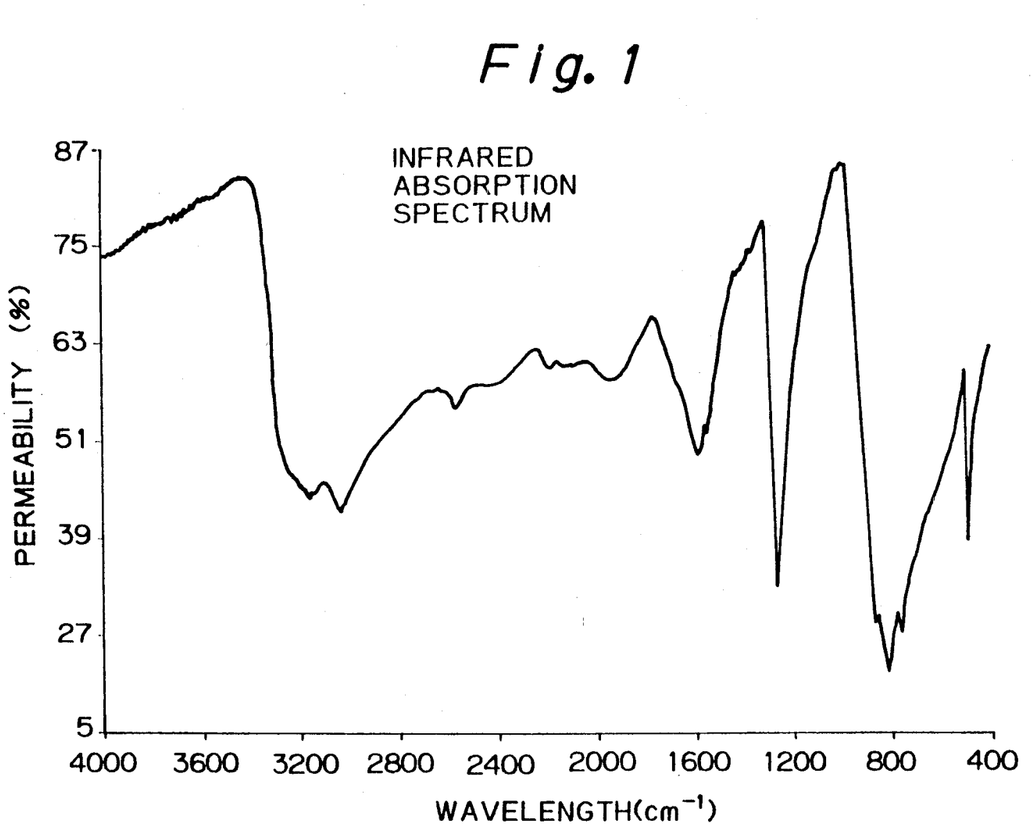
FIG. 1 is an infrared absorption spectrum of palladium tetramine molybdate usable for the present invention.
Figure 2:
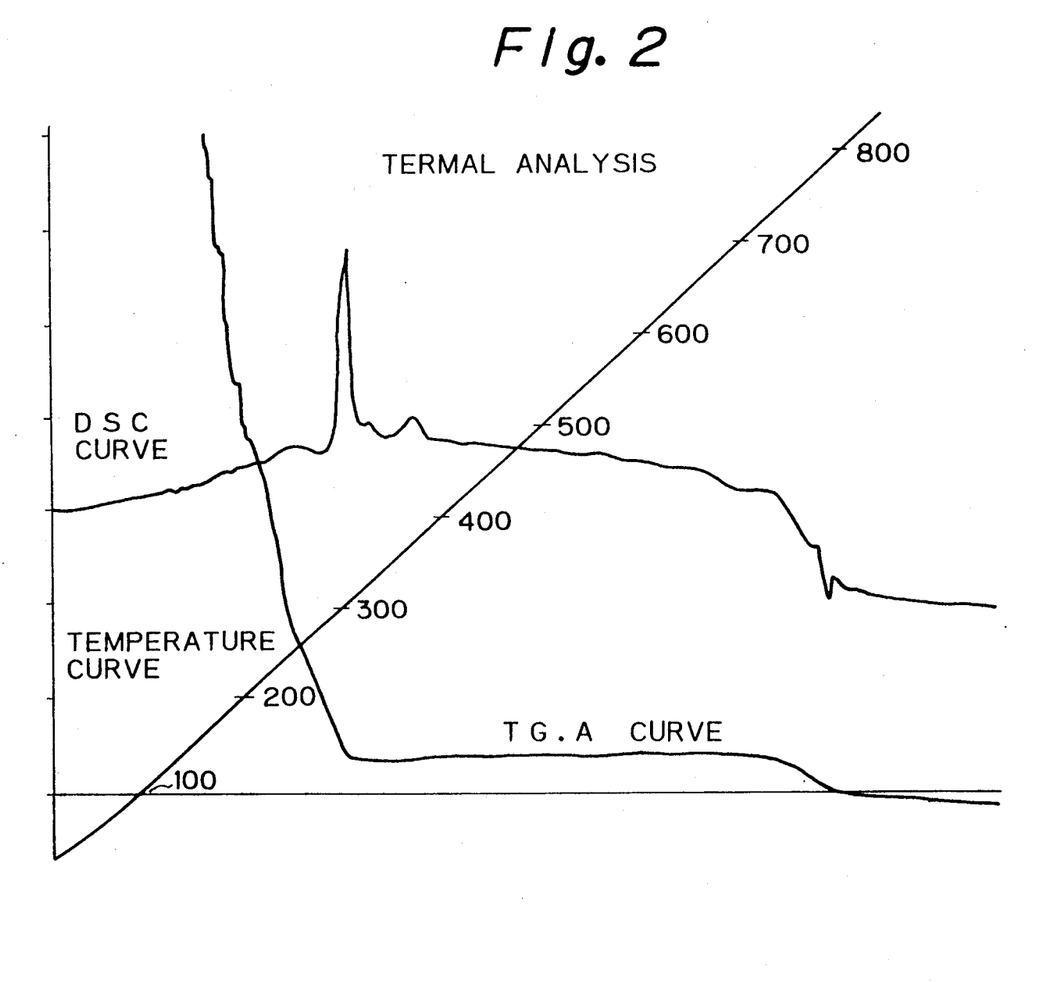
FIG. 2 shows thermal analysis curves of palladium tetramine molybdate.
Figure 3:
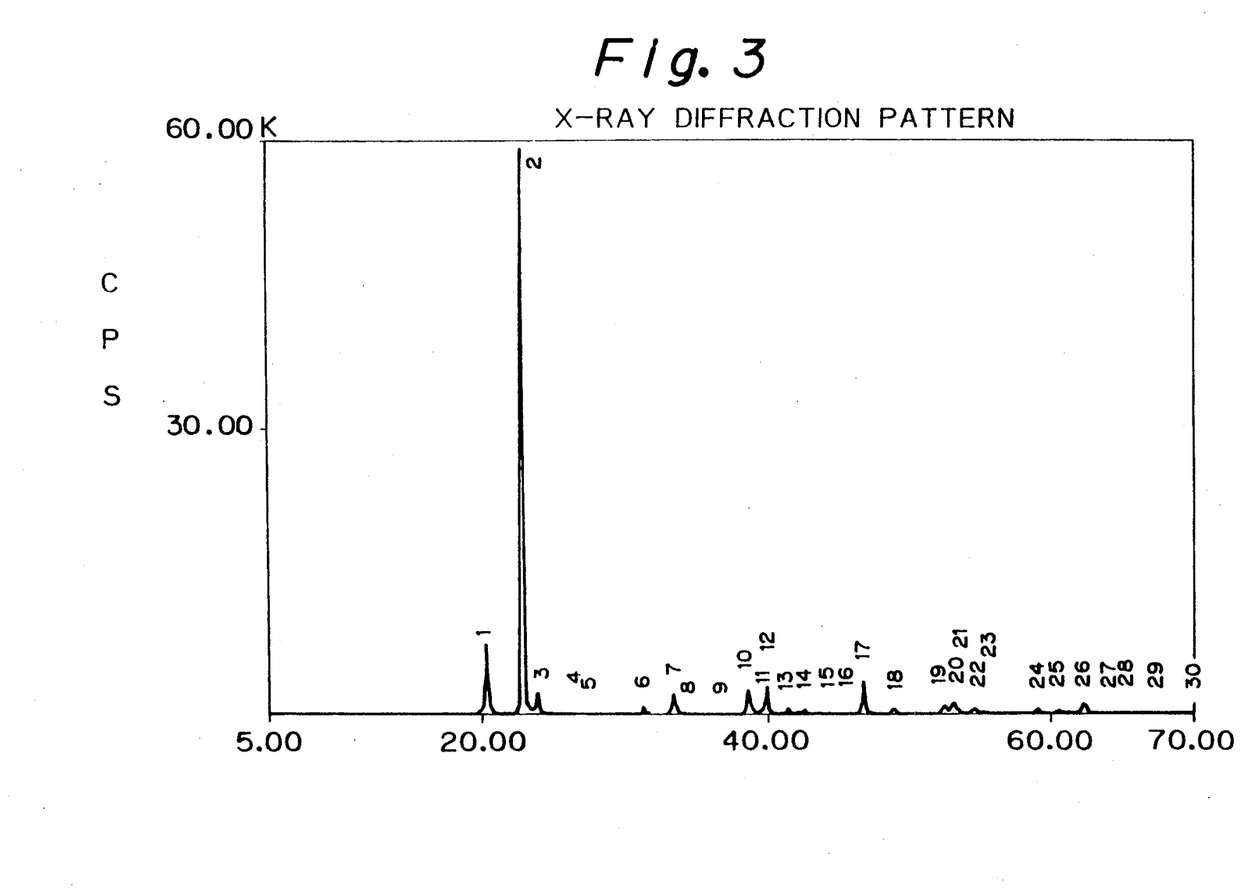
FIG. 3 is an X-ray diffraction pattern of palladium tetramine molybdate.

FIG. 1 shows an infrared absorption spectrum of the resultant crystal; FIG. 2 shows a thermal analysis curve of the resultant crystal; FIG. 3 shows an ultraviolet ray diffraction pattern of the resultant crystal; and, FIG. 4, 5 and 6 show ESCA spectral patterns of the resultant crystals.

In FIG. 1, the infrared absorption spectrum pattern shows specific absorptions at 3040 $cm^{-1}$ and 3160 $cm1^{-1}$ due to the NH bond, and other specific absorptions at from 3250 $cm^{-1}$ to 3300 $cm^{-1}$ due to the OH bond.

Figure 4:
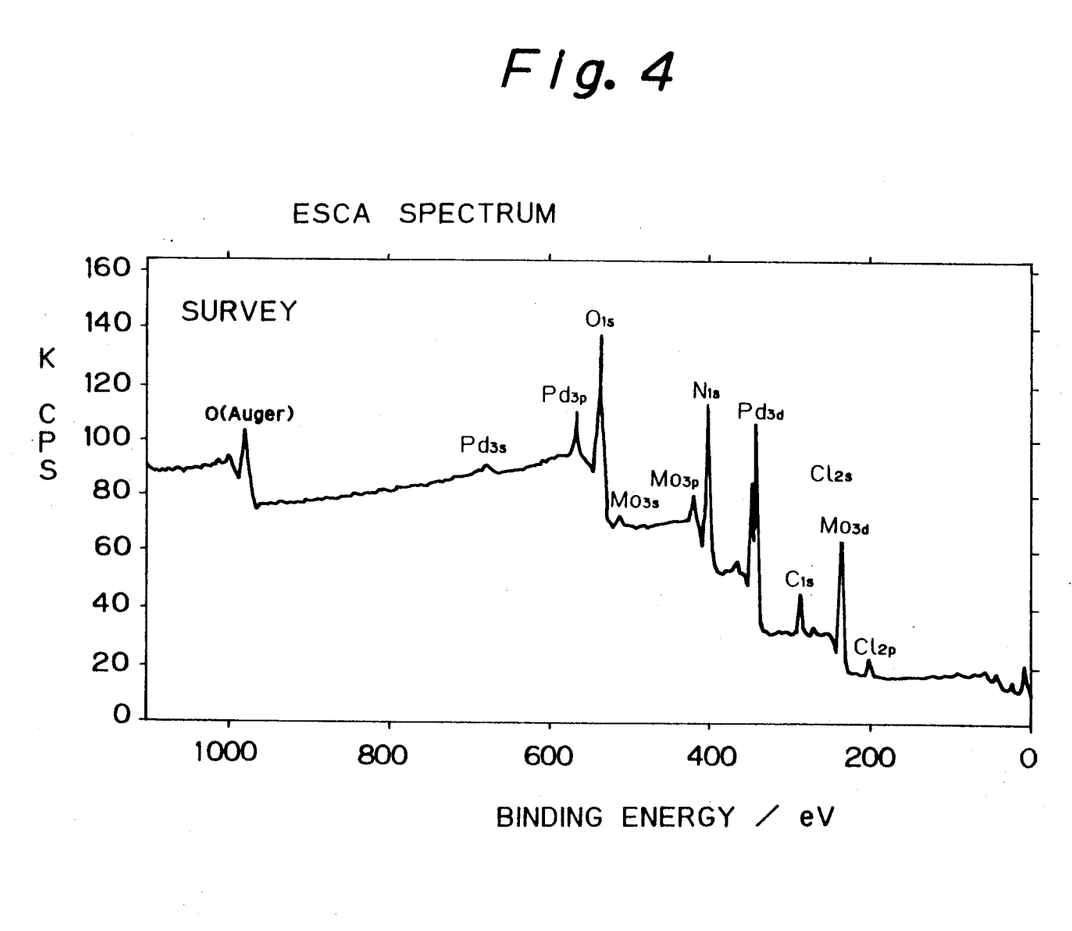
FIG. 4 is an ESCA spectrum of palladium tetramine molybdate.
Figure 5:
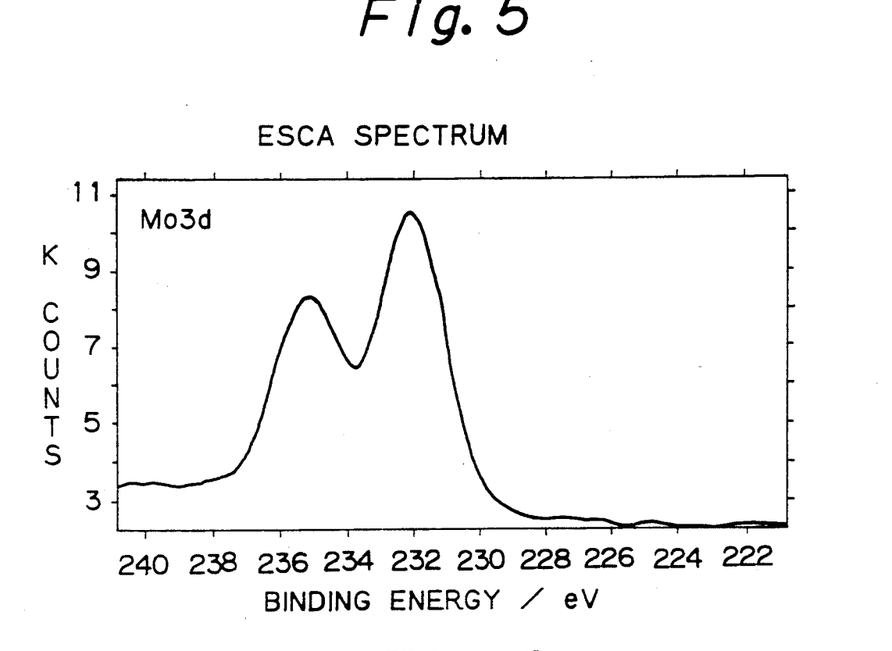
FIGS. 5 and 6 are partial enlargements of the ESCA spectrum of FIG. 4.
Figure 6:
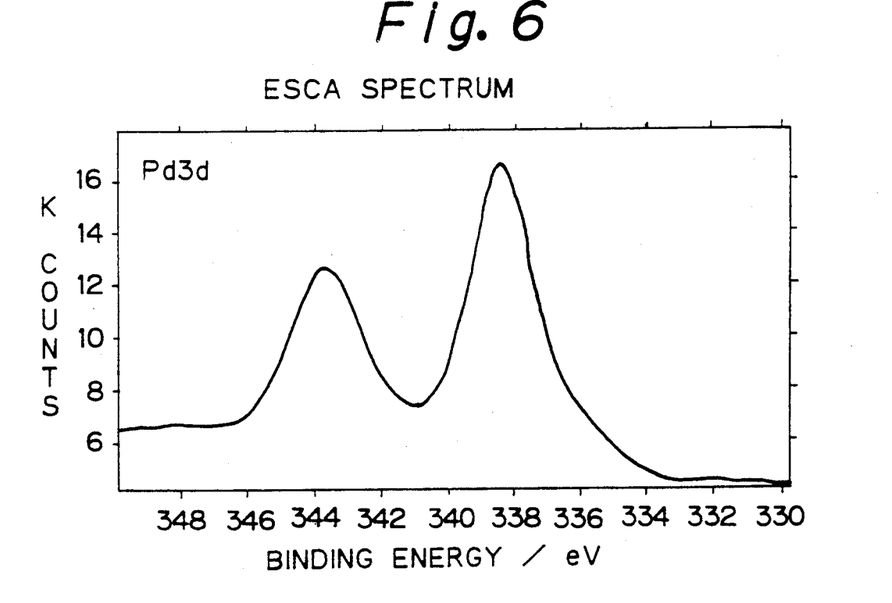

In FIGS. 4, 5 and 6, the ESCA spectrum patterns show spectra at 338.5 eV and 343.7 eV based on Pd-3d electrons belonging to Pd·$(NH_3)_4^{2+}$ and spectra at 232.0 eV and 235.0 eV based on Mo·3d electrons belonging to $MoO_4^{2-}$.

It was established from the above analysis that the resultant crystals consisted of palladium tetramine molybdate of the formula: $Pd(NH_3)_4MoO_4·H_2O$.

Preparation of Solid Catalyst

A solution of 0.66 g of palladium tetramine molybdate, 0.65 g of cupric chloride ($CuCl_2·2H_2O$) and 0.218 g of potassium chloride in 70 ml of an aqueous solution of 25% by weight of ammonia at a temperature of 80° C. to 90° C.

From the above-mentioned solution and 20 g of the activated carbon particles immersed in 50 ml of a 25% ammonia aqueous solution, a solid carrier was prepared in the same manner as in Example 1.

The palladium was contained in an amount of 1% based on the weight of the activated carbon particles (solid carrier).

The content ratio of Pd, Cu, Mo and K was 1 : 2 : 1 : 2.

Production of Dimethyl Carbonate

The above-mentioned solid catalyst in an amount of 2.5 ml was placed in a gas phase reaction tube having an inside diameter of 20 mm and equipped with an outside heating jacket. The reaction tube filled by the solid catalyst was fixed vertically and a heating medium consisting of a silicone oil was made to flow through the outside heating jacket to maintain the inside temperature of the reaction tube at a level of 120° C.

A mixed gas consisting of 8% by volume of methyl nitrite, 8% by volume of carbon monoxide, 3% by volume of nitrogen monoxide, 10% by volume of methyl alcohol and 71% by volume of nitrogen was fed into the reaction tube through a top end thereof at a space velocity (GHSV) of 8500 $hr^{-1}$ under the ambient atmospheric pressure. The methyl nitrite was produced from nitrogen monoxide, oxygen and methyl alcohol.

In the reaction tube, the methyl nitrite reacted with carbon monoxide in the presence of the solid catalyst.

The resultant reaction mixture discharged from the reaction tube through a bottom thereof was made to flow through methyl alcohol cooled with ice to collect the resultant reaction product. The collected reaction product was subjected to gas chromatography, and it was confirmed that, at 2 hours after the start of the reaction procedure, the space time yield (STY) of dimethyl carbonate was 436 g/l·hr, and at 6 hours after the start of the reaction procedure, the STY of dimethyl carbonate was 399 g/l·hr. Thus, the solid catalyst exhibited a catalytic activity reduction coefficient Da of 1.2 $hr^{-1}$

COMPARATIVE EXAMPLE 29

Preparation of a Solid Catalyst

The same solid catalyst preparation procedures as in Example 63 were carried out except that 0.66 of palladium, tetramine molybdate was heat-dissolved in 70 ml of an aqueous solution of 25% by weight of ammonia at a temperature of 80° C. to 90° C. to provide a catalyst component solution.

Separately, 20 g of activated carbon particles having a size of 0.5 to 0.7 mm were immersed and dispersed in 30 ml of a 25 weight % ammonia aqueous solution.

The above-mentioned palladium tetramine molybdate solution was added to the activated carbon particle dispersion, and the resultant mixture was left to stand for one hour at room temperature, heated at a temperature of 80° C. under a reduced pressure to remove water, and dried in a nitrogen atmosphere at a temperature of 200° C., to provide a solid catalyst containing palladium in an amount of 1% based on the weight of the solid carrier and having a gram atom equivalent ratio Pd : Mo was 1 : 1.

Production of Dimethyl Carbonate

This procedure as carried out in the same manner as in Example 63, except that the above-mentioned solid catalyst was used in place of the catalyst of Example 63.

The gas chromatographic analysis confirmed that the STY of dimethyl carbonate was 85 g/l·hr at 2 hours after the start of the reaction procedure and 50 g/l·hr at 6 hours after the start of the reaction procedure, and the catalytic activity reduction coefficient of the catalyst Da was 9.7 $hr^{-1}$.

EXAMPLE 64 to 70

In each of Examples 64 to 70, the same procedures as in Example 63 were carried out except that the catalyst had the empirical composition as shown in Table 5 and the gram atom equivalent ratio of the metals in the catalyst was as shown in Table 5.

Namely, the first and third catalyst components consisted of $Pd(NH_3)_4MoO_4·H_2O$; the second catalyst component consisted of $CuCl_2$, $CuSO_4$, $Cu(NO_3)_2$, $BiCl_3$, or $FeCl_3$, the fourth catalyst component consisted of KF, KCl, patassium acetate (KOAc), sodium acetate (NaOAc), $KH_2PO_4$ or $SrHPO_4$, and the solid carrier consisted of activated carbon, or MgO, as indicated in Table 5.

In the production of dimethyl carbonate, the initial STY of the dimethyl carbonate at 2 hours after the start of the reaction procedure, and the catalytic activity reduction coefficient of the catalyst, were as shown in Table 5.

COMPARATIVE EXAMPLE 30

The same procedures as in Example 63 were carried out except that the catalyst had the empirical composition as shown in Table 5 and the gram atom equivalent ratio of the metals in the catalyst was as shown in Table 5.

Namely, the first and second catalyst components consisted of palladium tetramine molybdate; the second catalyst component consisted of copper acetylacetone ($Cu(AcAc)_2$) the fourth catalyst component was not employed, and the solid carrier consisted of activated carbon as indicated in Table 5.

In the production of dimethyl carbonate the intial STY of the dimethyl carbonate at 2 hours after the start of the reaction procedure, and the catalytic activity reduction coefficient of the catalyst, were as shown in Table 5.

of methyl nitrite, 9% by volume of carbon monoxide, 4% by volume of nitrogen monoxide, 3% by volume of methyl alcohol and 75% by volume of nitrogen was fed to the reaction tube through a top end thereof at a space velocity (GHSV) of 2500 $hr^{-1}$ and the reaction was carried out under a pressure of 2.0 $kg/cm^2 G$.

The initial STY(Yo) of dimethyl carbonate at 2 hours after the start of the reaction procedure was 273 g/l·hr and the catalytic activity reduction coefficient Da was 0.5 $hr^{-1}$.

We claim:

1. A method of producing a carbonic acid diester, comprising the steps of:
    (A) catalytically reacting carbon monoxide with a nitrous acid ester in a gas phase in the presence of a solid catalyst composed of a solid carrier and a catalytic solid material carried on the carrier and comprising:

TABLE 5

| Example No. | | Empirical composition of catalyst | Gram atom equivalent ratio of metals in catalyst | Initial STY(*) Yo (g/l · hr) | Catalytic activity reduction coefficient Da ($hr^{-1}$) |
|---|---|---|---|---|---|
| Example | 64 | $Pd(NH_3)_4MoO_4 \cdot H_2O$—$CuCl_2$—KCl/C | Pd:Mo:Cu:K = 1:1:2:2 | 395 | 0.5 |
| | 65 | $Pd(NH_3)_4MoO_4 \cdot H_2O$—$CuSO_4$—NaOAc/C | Pd:Mo:Cu:Na = 1:1:2:2 | 184 | 0.4 |
| | 66 | $Pd(NH_3)_4MoO_4 \cdot H_2O$—$CuSO_4$—KOAc/C | Pd:Mo:Cu:K = 1:1:0.5:2 | 278 | 2.5 |
| | 67 | $Pd(NH_3)_4MoO_4 \cdot H_2O$—$Cu(NO_3)_2$—$KH_2PO_4$/C | Pd:Mo:Cu:K = 1:1:2:2 | 147 | 2.3 |
| | 68 | $Pd(NH_3)_4MoO_4 \cdot H_2O$—$CuCl_2$—KF/MgO | Pd:Mo:Cu:K = 1:1:2:1 | 426 | 1.8 |
| | 69 | $Pd(NH_3)_4MoO_4 \cdot H_2O$—$BiCl_3$—$SrHPO_4$/C | Pd:Mo:Bi:Sr = 1:1:1:4 | 382 | 0.7 |
| | 70 | $Pd(NH_3)_4MoO_4 \cdot H_2O$—$FeCl_3$—KOAc/C | Pd:Mo:Fe:K = 1:1:1:0.5 | 413 | 1.5 |
| Comparative Example | 30 | $Pd(NH_3)_4MoO_4 \cdot H_2O$—$Cu(AcAc)_2$/C | Pd:Mo:Cu = 1:1:2 | 2 | — |

Note: (*) . . . Space time yield in g/l · hr of dimethyl carbonate 2 hours after start of reaction procedure

EXAMPLE 71

The same procedures as in Example 63 were carried out except that the reaction temperature was changed from 120° C. to 100° C.

The initial STY(Yo) of dimethyl carbonate at 2 hours after the start of the reaction procedure was 314 g/l·hr and the catalytic activity reduction coefficient Da was 0.14 $hr^{-1}$.

EXAMPLE 72

The same procedures as in Example 63 were carried out except that the reaction temperature was changed from 120° C. to 140° C.

The initial STY(Yo) of dimethyl carbonate at 2 hours after the start of the reaction procedure was 793 g/l·hr and the catalytic activity reduction coefficient Da was 2.6 $hr^{-1}$.

EXAMPLE 73

The same procedures as in Example 1 were carried out except that in the mixed gas fed to the reaction tube, the methyl nitrite was replaced by ethyl nitrite and methyl alcohol was replaced by ethyl alcohol.

The initial STY(Yo) of dimethyl carbonate at 2 hours after the start of the reaction procedure was 567 g/l·hr and the catalytic activity reduction coefficient Da was 1.3 $hr^{-1}$.

EXAMPLE 74

The same procedures as in Example 63 were carried out except that the solid catalyst was placed in an amount of 8.5 ml in the reaction tube, and in the reaction procedure, a mixed gas consisting of 9% by volume (1) a first catalyst component consisting of at least one member selected from the group consisting of platinum group metals and compounds thereof;
(2) a second catalyst component consisting of at least one member selected from the group consisting of iron compounds, copper compounds, bismuth compounds, cobalt compounds, nickel compounds and tin compounds;
(3) a third catalyst component consisting of at least one member selected from the group consisting of vanadium compounds, molybdenum compounds and tungsten compounds; and
(4) a fourth catalyst component consisting of at least one member selected from alkali metal compounds and alkaline earth metal compounds; and
(B) collecting the resultant carbonic acid diester from a reaction mixture discharged from the catalytic reaction step (A).

2. The method as claimed in claim 1, wherein the nitrous acid ester is selected from the group consisting of nitrites of lower aliphatic monohydric alcohols having 1 to 4 carbon atoms, nitrites of cycloaliphatic monohydric alcohols and nitrites of aralkyl monohydric alcohols.

3. The method as claimed in claim 1, wherein the platinum group metal is selected from the group consisting of palladium, platinum, iridium, ruthenium and rhodium.

4. The method as claimed in claim 1, wherein the platinum group metal compound is selected from the group consisting of halides, nitrates, sulfates, phosphates, acetates, oxalates, and benzoates of the palladium group metals.

5. The method as claimed in claim 1, wherein the second catalyst component consists of at least one member selected from halides, nitrates, sulfates, phosphates and acetates of iron, copper, bismuth, cobalt, nickel and tin.

6. The method as claimed in claim 1, wherein the third catalyst component consists of at least one member selected from the group consisting of oxides, metal acids, metal salts of metal acids, and ammonium salts of metal acids of vanadium, molybdenum and tungsten.

7. The method as claimed in claim 1, wherein the fourth catalyst component consists of at least one member selected from halides of alkali metals and organic acid salts and phosphates of alkali metals and alkaline earth metals.

8. The method as claimed in claim 1, wherein the fourth catalyst component consists of at least one member selected from the group consisting of fluorides of alkali metals.

9. The method as claimed in claim 1, wherein the fourth catalyst component consists of at least one member selected from the group consisting of alkali metal salts and alkaline earth metal salts of organic acids.

10. The method as claimed in claim 9, wherein the organic acids are selected from the group consisting of formic acid and acetic acid.

11. The method as claimed in claim 1, wherein the fourth catalyst component consists of at least one member selected from chlorides of alkali metals.

12. The method as claimed in claim 1, wherein the fourth catalyst component consists of at least one member selected from the group consisting of phosphates of alkali metals and alkaline earth metals.

13. The method as claimed in claim 1, wherein the solid carrier comprises at least one member selected from the group consisting of diatomaceous earth, activated carbon, silicon carbide, titania, alumina and silica-alumina.

14. The method as claimed in claim 1, wherein the first catalyst component is present in an amount of from 0.1 to 10% by weight in terms of platinum group metal, based on the weight of the solid carrier.

15. The method as claimed in claim 1, wherein the second catalyst component is present in an amount in terms of the metal as used, of 0.1 to 50 gram atom equivalents per gram atom equivalent of the first catalyst component in terms of the platinum group metal contained therein.

16. The method as claimed in claim 1, wherein the third catalyst component is present in an amount in terms of the metal, of 0.1 to 20 gram atom equivalents, per gram atom equivalent of the first catalyst component in terms of the platinum group metal.

17. The method as claimed in claim 1, wherein the fourth catalyst component is present in an amount, in terms of the metal, of 0.1 to 20 gram atom equivalents, per gram atom equivalent of the first catalyst component in terms of the platinum group metal.

18. The method as claimed in claim 1, wherein the catalytic solid material is carried on the carrier by an impregnating, mix-kneading, depositing, evaporate-drying or coprecipitating method.

19. The method as claimed in claim 1, wherein the solid catalyst is in the form of fine particles having of a size of from 20 to 100 $\mu$m.

20. The method as claimed in claim 1, wherein the solid catalyst is in the form of coarse particles having a mesh size of 4 to 200.

21. The method as claimed in claim 1, wherein the solid catalyst is in the form of grains or shaped articles having a size of 1 to 30 mm.

22. The method as claimed in claim 1, wherein the catalytic reaction of carbon monoxide with the nitrous acid ester is carried out at a temperature of 0 to 200° C.

23. The method as claimed in claim 1, wherein the catalytic reaction of carbon monoxide with the nitrous acid ester is carried out under a pressure of from the ambient atmospheric pressure to 20 kg/cm$^2$G.

24. The method as claimed in claim 1, wherein, in the catalytic reaction step (A), carbon monoxide is present in a concentration of 5 to 20% by volume, and the nitrous acid ester is present in a concentration of 20% by volume or less.

25. The method as claimed in claim 1, wherein, in the catalytic reaction step (A), carbon monoxide is present in an amount of 0.1 to 10 moles per mole of the nitrous acid ester.

26. The method as claimed in claim 1, wherein, in the collection step (B), the reaction mixture discharged from the catalytic reaction step (A) is subjected to a cool-condensing procedure and the resultant carbonic acid diester is collected from a cool-condensing procedure product.

27. The method as claimed in claim 1, wherein palladium tetramine molybdate is used as the first and third catalyst components.

28. The method as claimed in claim 27, wherein the palladium tetramine molybdate is a reaction product of a molybdate with a palladium salt in a molar ratio of from 0.2 : 1 to 5.0 : 1 in an aqueous ammonia solution.

* * * * *